United States Patent
Blenis et al.

(10) Patent No.: US 6,372,467 B1
(45) Date of Patent: Apr. 16, 2002

(54) P54$^{S6K}$ AND P85$^{S6K}$ GENES, PROTEINS, PRIMERS, PROBES, AND DETECTION METHODS

(75) Inventors: John Blenis, Roslindale, MA (US); Kay K. Lee-Fruman, Hermosa Beach, CA (US); Calvin J. Kuo, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/430,564

(22) Filed: Oct. 29, 1999

Related U.S. Application Data

(60) Provisional application No. 60/106,141, filed on Oct. 29, 1998.

(51) Int. Cl.$^7$ .............................. C12N 9/00; C12N 9/12
(52) U.S. Cl. ....................................... 435/194; 435/183
(58) Field of Search .................................. 435/183, 194

(56) References Cited

U.S. PATENT DOCUMENTS 5,985,635 A    11/1999  Bandman et al. ........... 435/194

OTHER PUBLICATIONS

Kozma et al. Active baculovirus recombinant p70S6K and p85S6K produced as a function of the infectious response. Journal of Biological Chemistry, 1993, vol. 268:7134–7138, Apr. 1993.*

Alessi et al., "Phosphoinositide–dependent Protein Kinase 1 (PDK1) Phosphorylates and Activates the p70 S6 Kinase In Vivo and In Vitro," Curr. Biol. 8:69–81 (1998).

Banerjee et al., "Molecular Structure of a Major Insulin/Mitogen–Activated 70–kDa S6 Protein Kinase," Proc. Natl. Acad. Sci. USA 87:8550–8554 (1990).

Chou et al., "The 70 kDa S6 Kinase: Regulation of a Kinase with Multiple Roles in Mitogenic Signalling," Curr. Opin. Cell Biol. 7:806–814 (1995).

Grammer et al., "The p70$^{S6k}$ Signalling Pathway: A Novel Signalling System Involved in Growth Regulation," Cancer Surveys 27:271–292 (1996).

Grove et al., "Cloning and Expression of Two Human p70 S6 Kinase Polypeptides Differing Only at Their Amino Termini," Mol. Cell. Biol. 11:5541–5550 (1991).

Kapeller et al., "Phosphatidylinositol 3–Kinase," Bioessays 16:565–576 (1994).

Kawasome et al., "Targeted Disruption of p70$^{s6k}$ Defines its Role in Protein Synthesis and Rapamycin Sensitivity," Proc. Natl. Acad. Sci. USA 95:5033–5038 (1998).

Kozma et al., "Cloning of the Mitogen–Activated S6 Kinase from the Rat Liver Reveals an Enzyme of the Second Messenger Subfamily," Proc. Natl. Acad. Sci. USA 87:7365–7369 (1990).

Weng et al., "Phosphatidylinositol 3–Kinase Signals Activation of p70 S6 Kinase in situ through Site–specific p70 Phosphorylation," Proc. Natl. Acad. Sci. USA 92:5744–5748 (1995).

\* cited by examiner

*Primary Examiner*—Ponnathapuachuta Murthy
*Assistant Examiner*—Manjunath N. Rao
(74) *Attorney, Agent, or Firm*—Clark & Elbing LLP; Kristina Bieker-Brady

(57) ABSTRACT

Disclosed are novel mammalian kinases, p54$^{S6K}$ and p85$^{S6K}$. Also disclosed are methods for identifying compounds that modulate, or which are modulated by, p54$^{S6K}$ or p85$^{S6K}$. In addition, the invention discloses methods for diagnosing or treating a cellular proliferative disease.

10 Claims, 9 Drawing Sheets

FIG. 1A

```
GGCACGAGCGACGGGCCCGCGGGGCCGGCGCCGCCATGGCGGCCGTGTTTGATTTGGATTTGGAGACGGAGGAAGGCAGCGAGGGCGAGG
                                    M  A  A  V  F  D  L  D  L  E  T  E  E  G  S  E  G  E      90

GCGAGCCAGAGCTCAGCCCCGCGGACGCATGTCCCCTTGCCGAGTTGAGGGCAGCTGGCCTAGAGCCTGTGGGACACTATGAAGAGGTGG
 G  E  P  E  L  S  P  A  D  A  C  P  L  A  E  L  R  A  A  G  L  E  P  V  G  H  Y  E  E  V   180

AGCTGACTGAGACCAGCGTGAACGTTGGCCCAGAGCGCATCGGGCCCCACTGCTTTGAGCTGCTGCGTGTGCTGGGCAAGGGGGGCTATG
 E  L  T  E  T  S  V  N  V  G  P  E  R  I  G  P  H  C  F  E  L  L  R  V  L  G  K  G  G  Y   270

GCAAGGTGTTCCAGGTGCGAAAGGTGCAAGGCACCAACTTGGGCAAAATATATGCCATGAAAGTCCTAAGGAAGGCCAAAATTGTGCGCA
 G  K  V  F  Q  V  R  K  V  Q  G  T  N  L  G  K  I  Y  A  M  K  V  L  R  K  A  K  I  V  R   360

ATGCCAAGGACACAGCACACACACGGGCTGAGCGGAACATTCTAGAGTCAGTGAAGCACCCCTTTATTGTGGAACTGGCCTATGCCTTCC
 N  A  K  D  T  A  H  T  R  A  E  R  N  I  L  E  S  V  K  H  P  F  I  V  E  L  A  Y  A  F   450

AGACTGGTGGCAAACTCTACCTCATCCTTGAGTGCCTCAGTGGTGGCGAGCTCTTCACGCATCTGGAGCGAGAGGGCATCTTCCTGGAAG
 Q  T  G  G  K  L  Y  L  I  L  E  C  L  S  G  G  E  L  F  T  H  L  E  R  E  G  I  F  L  E   540

ATACGGCCTGCTTCTACCTGGCTGAGATCACGCTGGCCCTGGGCCATCTCCACTCCCAGGGCATCATCTACCGGGACCTCAAGCCCGAGA
 D  T  A  C  F  Y  L  A  E  I  T  L  A  L  G  H  L  H  S  Q  G  I  I  Y  R  D  L  K  P  E   630

ACATCATGCTCAGCAGCCAGGGCCACATCAAACTGACCGACTTTGGACTCTGCAAGGAGTCTATCCATGAGGGCGCCGTCACTCACACCT
 N  I  M  L  S  S  Q  G  H  I  K  L  T  D  F  G  L  C  K  E  S  I  H  E  G  A  V  T  H  T   720

TCTGCGGCACCATTGAGTACATGGCCCCTGAGATTCTGGTGCGCAGTGGCCACAACCGGGCTGTGGACTGGTGGAGCCTGGGGGCCCTGA
 F  C  G  T  I  E  Y  M  A  P  E  I  L  V  R  S  G  H  N  R  A  V  D  W  W  S  L  G  A  L   810

TGTACGACATGCTCACTGGATCGCCGCCCTTTACCGCAGAGAACCGGAAGAAAACCATGGATAAGATCATCAGGGGCAAGCTGGCACTGC
 M  Y  D  M  L  T  G  S  P  P  F  T  A  E  N  R  K  K  T  M  D  K  I  I  R  G  K  L  A  L   900

CCCCTACCTCACCCCAGATGCCCGGGACCTTGTCAAAAAGTTTCTGAAACGGAATCCCAGCCAGCGGATTGGGGGTGGCCCAGGGGATG
 P  P  Y  L  T  P  D  A  R  D  L  V  K  K  F  L  K  R  N  P  S  Q  R  I  G  G  G  P  G  D   990

CTGCTGATGTGCAGAGACATCCCTTTTTCCGGCACATGAATTGGGACGACCTTCTGGCCTGGCGTGTGGACCCCCCTTTCAGGCCCTGTC
 A  A  D  V  Q  R  H  P  F  F  R  H  M  N  W  D  D  L  L  A  W  R  V  D  P  P  F  R  P  C  1080

TGCAGTCAGAGGAGGACGTGAGCCAGTTTGATACCCGCTTCACACGGCAGACGCCGGTGGACAGTCCTGATGACACAGCCCTCAGCGAGA
 L  Q  S  E  E  D  V  S  Q  F  D  T  R  F  T  R  Q  T  P  V  D  S  P  D  D  T  A  L  S  E  1170

GTGCCAACCAGGCCTTCCTGGGCTTCACATACATGGCGCCGTCTGTCCTGGACAGCATCAAGGAGGGCTTCTCCTTCCAGCCCAAGCTGC
 S  A  N  Q  A  F  L  G  F  T  Y  M  A  P  S  V  L  D  S  I  K  E  G  F  S  F  Q  P  K  L  1260

GCTCACCCAGGCGCCTCAACAGTAGCCCCCGGGTCCCCGTCAGCCCCCTCAAGTTCTCCCCTTTTGAGGGGTTTCGGCCCAGCCCCAGCC
 R  S  P  R  R  L  N  S  S  P  R  V  P  V  S  P  L  K  F  S  P  F  E  G  F  R  P  S  P  S  1350

TGCCGGAGCCCACGGAGCTACCTCTACCTCCACTCCTGCCACCGCCGCCGCCCTCGACCACCGCCCCTCTCCCCATCCGTCCCCCCTCAG
 L  P  E  P  T  E  L  P  L  P  P  L  L  P  P  P  P  P  S  T  T  A  P  L  P  I  R  P  P  S  1440

GGACCAAGAAGTCCAAGAGGGGCCGTGGGCGTCCAGGGCGCTAGGAAGCCGGGTGGGGGTGAGGGTAGCCCTTGAGCCCTGTCCCTGCGG
 G  T  K  K  S  K  R  G  R  G  R  P  G  R                                                   1530

CTGTGAGAGCAGCAGGACCCTGGGCCAGTTCCAGAGACCTGGGGGTGTGTCTGGGGGTGGGGTGTGAGTGCGTATGAAAGTGTGTGTCTG
                                                                                            1620

CTGGGGCAGCTGTGCCCCTGAATCATGGGCACGGAGGGCCGCCCGCCACACCCCGCGCTCAACTGCTCCCGTGGAAGATTAAAGGGCTGA
                                                                                            1710

ATCATGAAAAAAAAAAAAAAAA
                      1732
```

P54$^{S6K}$ AND P85$^{S6K}$ GENES, PROTEINS, PRIMERS, PROBES, AND DETECTION METHODS

CROSS REFERENCE TO RELATED APPLICATIONS

This application claims priority from U.S. Provisional Application Ser. No. 60/106,141, filed Oct. 29, 1998.

STATEMENT AS TO FEDERALLY SPONSORED RESEARCH

This invention was made in part with Government funding, and the Government therefore has certain rights in the invention.

BACKGROUND OF THE INVENTION

The invention relates to the diagnosis and treatment of conditions associated with cell proliferation.

The control of cell proliferation is a fundamental issue in medicine. Cell proliferation is regulated by the formation and dissociation of multiple protein complexes, the components of which often use post-translational modifications as an additional control mechanism. Many diseases result from inappropriate cell proliferation, including cancer. Methods and reagents to modulate cell proliferation would have the potential to yield new treatments for cancer, major opportunistic infections, immune disorders, certain cardiovascular diseases, and inflammatory disorders.

SUMMARY OF THE INVENTION

In general, the invention features a substantially pure nucleic acid (for example, genomic DNA, cDNA, synthetic DNA, mRNA, or antisense RNA) encoding a p54$^{S6K}$ or p85$^{S6K}$ polypeptide, as defined below.

In a preferred embodiment, the substantially pure nucleic acid encoding a p54$^{S6K}$ or p85$^{S6K}$ polypeptide is mammalian DNA. More preferably, the substantially pure nucleic acid encoding a p54$^{S6K}$ or p85$^{S6K}$ polypeptide is human DNA. In another embodiment, the invention features a DNA sequence substantially identical to, or which hybridizes with high stringency to, the DNA sequence shown in FIG. 1A or 5 (SEQ ID NO: 1).

In another embodiment, the invention features DNA encoding fragments of p54$^{S6K}$ or p85$^{S6K}$ polypeptides. In preferred embodiments, the fragments include the C-terminal and N-terminal regions of p54$^{S6K}$ or p85$^{S6K}$ that are distinct from p70$^{S6k}$, the catalytic domain of p54$^{S6K}$ or p85$^{S6K}$, the linker domain, the proline rich domain, or the acidic region of p54$^{S6K}$ or p85$^{S6K}$. In preferred embodiments, the fragment contains amino acids 1-65 (N-terminal domain), 6-23 (acidic domain), 65-332 (catalytic domain), 332-397 (linker domain), 398-482 (C-terminal domain), or 446-467 (proline rich domain) of p54$^{S6K}$ (SEQ ID NOs: 4–10). In other preferred embodiments, the fragment contains amino acids 14-78 (N-terminal domain), 19-36 (acidic domain), 78-345 (catalytic domain), 345-410 (linker domain), 411-495 (C-terminal domain), or 495-480 (proline rich domain) of p85$^{S6K}$ (SEQ ID NOs: 10–15). In another embodiment, the invention features nucleic acids that bind with high stringency to SEQ ID NOs: 1 or 2.

In another aspect, the invention features a substantially pure polypeptide having a sequence substantially identical to SEQ ID NOs: 2 or 3. In a preferred embodiment, the substantially pure polypeptide has an acidic region at its N-terminus and a central catalytic region. In another the preferred embodiment, the substantially pure polypeptide has a post-translational modification In other aspects of the invention, a substantially pure p54$^{S6K}$ or p85$^{S6K}$ polypeptide has one or more amino acids changed by natural or artificial means, the p54$^{S6K}$ or p85$^{S6K}$ polypeptide is p54$^{S6K}$ KR or p85$^{S6K}$ KR, or the p54$^{S6K}$ or p85$^{S6K}$ polypeptide is a fusion with a heterologous polypeptide, for example, glutathione-S-transferase (GST) or influenza hemagglutinin (HA), relative to the wild-type p54$^{S6K}$ or p85$^{S6K}$ sequence shown in FIG. 1A or FIG. 5.

In another aspect, the invention features fragments of p54$^{S6K}$ or p85$^{S6K}$ polypeptides. In a preferred embodiment, the fragment is a peptide comprising a C-terminal sequence of p54$^{S6K}$ or p85$^{S6K}$ that is distinct from p70$^{S6k}$ or p85$^{S6K}$. In another embodiment, the fragment comprises a N-terminal sequence of p54$^{S6K}$ or p85$^{S6K}$ that is distinct from p70$^{S6k}$. In another embodiment, the fragment comprises the catalytic domain of p54$^{S6K}$ or p85$^{S6K}$. In another embodiment, the fragment comprises the acidic region of p54$^{S6K}$ or p85$^{S6K}$ In another embodiment, the fragment comprises the linker domain of p54$^{S6K}$ or p85$^{S6K}$. In another embodiment, the fragment comprises the proline rich region of p54$^{S6K}$ or p85$^{S6K}$. In another embodiment, the fragment contains a post-translational modification of p54$^{S6K}$ or p85$^{S6K}$. In yet another embodiment, the fragment is a fragment of p54$^{S6K}$ KR or p85$^{S6K}$ KR. In still another embodiment, the fragment is fused to a heterologous polypeptide. In preferred embodiments, the fragment contains amino acids 1-65 (N-terminal domain), 6-23 (acidic domain), 65-332 (catalytic domain), 332-397 (linker domain), 398-482 (C-terminal domain), or 446-467 (proline rich domain) of p54$^{S6K}$ (SEQ ID NOs: 4–9). In other preferred embodiments, the fragment contains amino acids 14-78 (N-terminal domain), 19-36 (acidic domain), 78-345 (catalytic domain), 345-410 (linker domain), 411-495 (C-terminal domain), or 495-480 (proline rich domain) of p85$^{S6K}$ (SEQ ID NOs: 10–15).

In another aspect, the invention features an antibody that specifically binds to a p54$^{S6K}$ or p85$^{S6K}$ polypeptide, a p54$^{S6K}$ or p85$^{S6K}$ polypeptide fragment, or a post-translational modification of a p54$^{S6K}$ or p85$^{S6K}$ polypeptide. In a preferred embodiment, the antibody is Ab#167.

In another aspect, the invention features a cell line having a genetically engineered null mutation in a p54$^{S6K}$ or p85$^{S6K}$ gene. In a preferred embodiment, the cell line is an embryonic stem cell line. If the cell is in a mammal, the mammal is preferably a non-human.

In another aspect, the invention features a cell line, genetically engineered to overexpress a p54$^{S6K}$ or p85$^{S6K}$ polypeptide. In a preferred embodiment, the cell line is a tumor cell line.

In another aspect, the invention features a non-human transgenic animal, or embryo thereof, with a knockout mutation in the p54$^{S6K}$ or p85$^{S6K}$ gene. In a related aspect, the invention features a non-human transgenic animal with additional copies of p54$^{S6K}$ or p85$^{S6K}$ nucleic acids added to its genome. In a preferred embodiment of these aspects, the non-human transgenic animal is a rodent, more preferably a mouse. In a preferred embodiment the animal has a knockout mutation in both genes.

In other aspects, the invention features methods of identifying a compound which modulates, or whose activity is modulated by, p54$^{S6K}$ or p85$^{S6K}$ biological activity involving: a) providing a cell expressing a p54$^{S6K}$ or p85$^{S6K}$ polypeptide, or a lysate from the cell expressing a p54$^{S6K}$ or p85$^{S6K}$ polypeptide, or a transgenic animal expressing a p54$^{S6K}$ or p85$^{S6K}$ polypeptide; b) exposing the cell, lysate, or transgenic animal to the test compound; c) assaying for a modulation in p54$^{S6K}$ or p85$^{S6K}$ biological activity; and d) comparing the modulation in p54$^{S6K}$ or p85$^{S6K}$ biological activity to that of a cell, lysate, or transgenic animal which did not receive the test compound, wherein a modulation of p54$^{S6K}$ or p85$^{S6K}$ biological activity identifies a test compound. In a preferred embodiment the biological activity is assayed by measuring p54$^{S6K}$ or p85$^{S6K}$ phosphorylation, p54$^{S6K}$ or p85$^{S6K}$ kinase activity, p54$^{S6K}$ or p85$^{S6K}$ polypeptide or nucleic acid levels, or cell proliferation. In another preferred embodiment, p54 or p85$^{S6K}$ biological activity is measured by using S6 or BRCA1 as a substrate. In other embodiments, the cell is induced or genetically engineered to express the p54$^{S6K}$ or p85$^{S6K}$ polypeptide. In a preferred embodiment the cell is a tumor cell and/or the p54$^{S6K}$ or p85$^{S6K}$ polypeptide is p54$^{S6K}$ KR or p85$^{S6K}$ KR. In another preferred embodiment, the test compound is BRCA1. In a related aspect, the cell may express an altered p54$^{S6K}$ or p85$^{S6K}$, as described herein before (e.g., a fusion, fragment, etc.), In other embodiments, the cell is exposed to a stimulus which could include serum or insulin. In other embodiments the cell is exposed to an inhibitor which could include rapamycin or wortmannin.

In another aspect, the invention features a method of diagnosing an increased likelihood of a cell proliferative disease in a subject. The method includes detecting the level of p54 or p85$^{S6K}$ gene expression in the subject. In preferred embodiments of this aspect, detection of the level of p54$^{S6K}$ or p85$^{S6K}$ gene expression is done by nucleic acid hybridization, including Northern blotting, Southern blotting, Western blotting, far-Western blotting, or DNA-mRNA hybridization. In another embodiment the subject is a human.

In a final aspect, the invention features a therapeutic composition comprising as an active ingredient a p54$^{S6K}$ or p85$^{S6K}$ polypeptide or nucleic acid, the active ingredient being formulated in a physiologically acceptable carrier. In a preferred embodiment, the p54$^{S6K}$ or p85$^{S6K}$ nucleic acid is in the context of a vector, more preferably a gene therapy vector.

By "substantially pure nucleic acid" is meant nucleic acid that is free of the substances that naturally accompany it. In the case of DNA, it would mean DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. In the case of RNA, it would include mRNA free of associated proteins and nucleic acids.

By "p54$^{S6K}$" is meant any gene or polypeptide, which is not p70$^{S6k}$, which hybridizes with high stringency to SEQ ID NO: 1 or and has p54$^{S6K}$ biological activity.

By "p85$^{S6K}$" is meant any gene or polypeptide, which is not p70$^{S6k}$, which hybridizes with high stringency to a gene encoding the polypeptide of SEQ ID NO: 3 and has p85$^{S6K}$ biological activity.

By "high stringency" is meant conditions that are commonly understood in the art as stringent. An exemplary set of high stringency conditions include a temperature of 60–70° C., (preferably about 65° C.) and a salt concentration of 0.70 M to 0.80 M (preferably about 0.75 M). Further exemplary conditions include, hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 5×Denhardt's solution, sonicated salmon sperm DNA (50 g/ml), 0.1% SDS, and 10% dextran sulfate at 42° C., with washes at 42° C. in 0.2×SSC and 0.1% SDS. Further examples of stringent conditions can be found in Sambrook, Fritsch and Maniatis, *Molecular Cloning: A Laboratory Manual* (2d ed.), Cold Spring Harbor Press, 1989, or Ausubel et al., *Current Protocols in Molecular Biology*, John Wiley & Sons, New York, N.Y., 1994).

By "polypeptide" or "polypeptide fragment" is meant any chain of more than two amino acids, regardless of post-translational modification (e.g., glycosylation or phosphorylation), constituting all or part of a naturally occurring polypeptide, or constituting a non-naturally occurring polypeptide.

By "substantially pure p54$^{S6K}$ polypeptide" is meant a p54$^{S6K}$ polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, p54$^{S6K}$ polypeptide. A substantially pure p54$^{S6K}$ polypeptide may be obtained, for example, by extraction from a natural source; by expression of a recombinant nucleic acid encoding an p54$^{S6K}$ polypeptide; or by chemically synthesizing the protein. Purity can be measured by any appropriate method, e.g., column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cells from which is naturally originates will be substantially free from its naturally associated components. Accordingly, substantially pure p54$^{S6K}$ polypeptides include those derived from eukaryotic organisms but synthesized in *E. coli* or other prokaryotes.

By "substantially pure p85$^{S6K}$ polypeptide" is meant a p85$^{S6K}$ polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, p85$^{S6K}$ polypeptide. A substantially pure p85$^{S6K}$ polypeptide may be obtained, for example, by extraction from a natural source; by expression of a recombinant nucleic acid encoding an p85$^{S6K}$ polypeptide; or by chemically synthesizing the protein. Purity can be measured by any appropriate method, e.g., column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cells from which is naturally originates will be substantially free from its naturally associated components. Accordingly, substantially pure $p85^{S6K}$ polypeptides include those derived from eukaryotic organisms but synthesized in E. coli or other prokaryotes.

By "substantially identical" is meant a polypeptide or nucleic acid exhibiting at least 85%, more preferably 90%, and most preferably 95% identity to a reference amino acid sequence (for example, the amino acid sequence described herein) or nucleic acid sequence (for example, the nucleic acid sequence described herein). For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 60 nucleotides, preferably at least 75 nucleotides, and more preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, and/or other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "specifically binds" is meant an antibody which recognizes and binds a protein, but which does not substantially recognize and bind other molecules in a sample, e.g., a biological sample, which naturally includes protein.

By "post-translational modification" is meant any changes to the polypeptide during or after synthesis. These modifications may include phosphorylation and glycosylation. Post-translational modifications may be naturally occurring (such as during synthesis within a cell), or artificially generated (such as by recombinant or chemical means).

By "null cell line" is meant a cell line that does not express a $p54^{S6K}$ or does not express a $p85^{S6K}$ polypeptide or which expresses a $p54^{S6K}$ or $p85^{S6K}$ polypeptide fragment having decreased biological activity. Preferably the cell line lacks detectable biological activity for said polypeptide. The cell line may be created by genetic engineering such that there is a mutation that makes a $p54^{S6K}$ or $p85^{S6K}$ polypeptide that has no detectable biological activity, or prevents the cell from making a $p54^{S6K}$ or $p85^{S6K}$ polypeptide.

By "overexpressing" is meant a cell line that expresses a $p54^{S6K}$ or $p85^{S6K}$ polypeptide or a $p54^{S6K}$ or $p85^{S6K}$ polypeptide fragment at a level at least 10% higher than the level of endogenous expression. This would include cells that express $p54^{S6K}$ or $p85^{S6K}$ either transiently, or stably incorporated into their genome. It would also include both prokaryotic and eukaryotic cells.

By "test compound" is meant a chemical, be it naturally-occurring or artificially-derived, that is surveyed for its ability to modulate $p54^{S6K}$ or $p85^{S6K}$ biological activity, by employing one of the assay methods described herein. Compounds may include, for example, polypeptides, synthesized organic molecules, naturally occurring organic molecules, nucleic acid molecules, and components thereof.

By "modulates" is meant changes, either by increase or decrease.

By "$p54^{S6K}$ biological activity" is meant any activity of $p54^{S6K}$ found in cells. This includes the levels of $p54^{S6K}$ nucleic acids or polypeptides, $p54^{S6K}$ phosphorylation, $p54^{S6K}$ kinase activity towards a variety of substrates, the inhibition of $p54^{S6K}$ activity by natural or artificial compounds, and the effect of $p54^{S6K}$ on substrates. This also includes the effect of $p54^{S6K}$ on cell proliferation and cell cycle.

By "$p85^{S6K}$ biological activity" is meant any activity of $p85^{S6K}$ found in cells. This includes the levels f $p85^{S6K}$ nucleic acids or polypeptides, $p85^{S6K}$ phosphorylation, $p85^{S6K}$ kinase activity towards a variety of substrates, the inhibition of $p85^{S6K}$ activity by natural or artificial compounds, and the effect of $p85^{S6K}$ on substrates. This also includes the effect of $p85^{S6K}$ on cell proliferation and cell cycle.

By "exposing" is meant allowing contact between an animal, cell, lysate or extract derived from a cell, or molecule derived from a cell, and a compound.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammals (e.g., rodents such as rats or mice) and the DNA (transgene) is inserted by artifice into the nuclear genome.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion, or is a frameshift mutation that creates a stop codon.

By "assaying" is meant analyzing the effect of a treatment or exposure, be it chemical or physical, administered to whole animals or cells. The material being analyzed may be an animal, a cell, a lysate or extract derived from cell, or a molecule derived from a cell. The analysis may be, for example, cell proliferation, cell morphology, or tumor formation. Techniques used in the analysis may include SDS polyacrylamide gel electrophoresis, in vitro kinase reactions, immunoprecipitation, etc.

By "substrate" is meant a molecule whose activity is modulated by $p54^{S6K}$ or $p85^{S6K}$ in vivo or in vitro. Substrates may include S6 and BRCA1. Preferably, a substrate is a molecule that has a phosphorylation state which is modified by $p54^{S6K}$ or $p85^{S6K}$ protein.

By "antisense," as used herein in reference to nucleic acids, is meant a nucleic acid sequence that is complementary to the coding strand of a gene, preferably, a $p54^{S6K}$ or $p85^{S6K}$ gene.

By "detecting the level of p54$^{S6K}$ gene expression" is meant detecting the levels of p54$^{S6K}$ polypeptides or nucleic acids. The detection would be relative to normal samples from patients without the cell proliferative disease.

By "detecting the level of p85$^{S6K}$ gene expression" is meant detecting the levels of p85$^{S6K}$ polypeptides or nucleic acids. The detection would be relative to normal samples from patients without the cell proliferative disease.

The invention provides methods and reagents for the diagnosis and treatment of diseases caused by inappropriate cell proliferation. These disorders can be treated, using the methods described herein, in a variety of ways including small molecules, gene therapy, antisense oligonucleotides and protein replacement. Additionally, they can have potential diagnostic/disease management applications as prognostic markers or predisposition indicators of certain cancers. Other features and advantages of the invention will be apparent from the detailed description of the invention, and from the claims.

BRIEF DESCRIPTION OF THE DRAWINGS

FIG. 1A shows the nucleotide sequence (SEQ ID NO: 1) and the deduced amino acid sequence (SEQ ID NO: 2) f p54$^{S6K}$. The 1732 nucleotides of p54$^{S6K}$ contains one open reading frame that encodes a protein of 482 amino acids (SEQ ID NO: 2). Multiple sequencing of clones isolated from the library as well as the examination of p54$^{S6K}$ EST clones show that seven of the clones have T at the nucleotide position 1294 (encoding valine at amino acid position 420), whereas four contain C at the position 1294 (encoding alanine at 420). Three clones isolated from Jurkat library (including the two full-length clones) have A at the nucleotide position at 1203 (encoding methionine at amino acid position 390), whereas one partial clone isolated from Jurkat library and four EST entries had G at the nucleotide position at 1203 (encoding valine at 390).

FIG. 5 shows a comparison between the deduced amino acid sequence of p70$^{S6K}$ (top line; SEQ ID NO: 16) and p85$^{S6K}$ (bottom line; SEQ ID NO: 3). p85$^{S6K}$ contains one open reading frame that encodes a protein of 495 amino acids.

DETAILED DESCRIPTION OF THE INVENTION

Figure 1B:
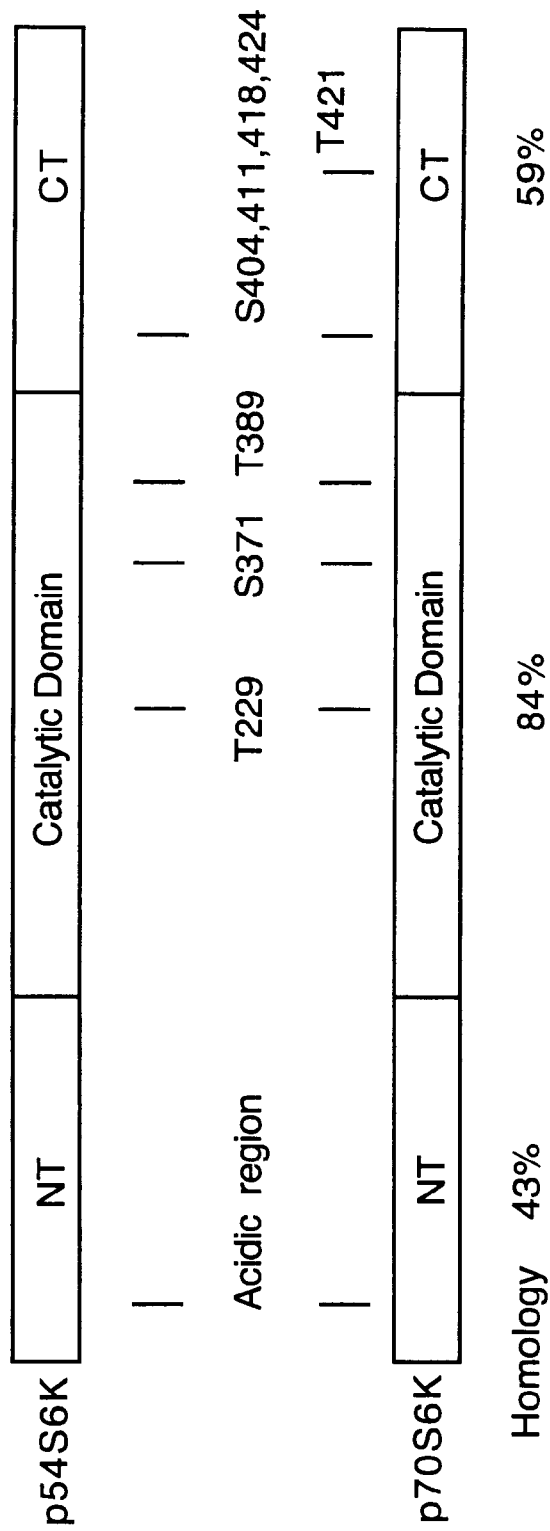
FIG. 1B is a schematic representation of the structural similarities between p54$^{S6K}$ and p70$^{S6K}$. Different domains of the proteins as well as the conserved amino acid sequences are shown. The degree of homology between the amino acid sequences of the two proteins are also shown.

We have discovered new mammalian protein kinases, p54$^{S6K}$ and p85$^{S6K}$, involved in cell proliferation. p54$^{S6K}$ activity is regulated by mitogens and phosphatidylinositol 3-kinase and inhibited by wortmannin and the inmunosuppressant rapamycin. We provide the amino acid sequences for $p54^{S6K}$ and $p85^{S6K}$ in FIGS. 1A and 5. $p54^{S6K}$, which has a molecular weight of 54 kDa, is ubiquitously expressed in human tissue. Characterization of the $p54^{S6K}$ protein, by the construction of kinase-dead mutants as well as other techniques, shows that it has intrinsic protein kinase activity, as well as being phosphorylated itself. $p85^{S6K}$ is a novel isoform of $p54^{S6K}$.

$p54^{S6K}$ and $p85^{S6K}$ Protein Expression $p54^{S6K}$ and $p85^{S6K}$ genes may be expressed in both prokaryotic and eukaryotic cell types. Using the techniques described herein, cell lines overexpressing $p54^{S6K}$ or $p85^{S6K}$ proteins may be made. Under some circumstances, it may be desirable to express the protein under control of an inducible promoter for the purposes of protein production.

In general, $p54^{S6K}$ or $p85^{S6K}$ proteins according to the invention may be produced by transformation of a suitable host cell with all or part of a $p54^{S6K}$-or $p85^{S6K}$, encoding cDNA fragment, respectively, in a suitable expression vehicle.

Those skilled in the field of molecular biology will understand that any of a wide variety of expression systems may be used to provide the recombinant protein. The precise host cell used is not critical to the invention. The $p54^{S6K}$ or $p85^{S6K}$ protein may be produced in a prokaryotic host (e.g., *E. coli*) or in a eukaryotic host (e.g., *Saccharomyces cerevisiae*, insect cells, e.g., Sf21 cells, or mammalian cells, e.g., HEK 293, COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al., (supra); expression vehicles may be chosen from those provided, e.g., in *Cloning Vectors: A Laboratory Manual* (P. H. Pouwels et al., 1985, Supp. 1987).

Alternatively, a $p54^{S6K}$ or $p85^{S6K}$ protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the protein is cloned into an expression vector which includes the dihydrofolate reductase (DHFR) gene. Integration of the plasmid and, therefore, the protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification. In addition, tumor cell lines overexpressing $p54^{S6K}$ or $p85^{S6K}$ proteins, or fragments of $p54^{S6K}$ or $p85^{S6K}$ proteins, may also be made.

Once the recombinant $p54^{S6K}$ or $p85^{S6K}$ protein is expressed, it is isolated, e.g., using affinity chromatography. In one example, an anti-$p54^{S6K}$ or $p85^{S6K}$ protein antibody (e.g., produced as described herein) may be attached to a column and used to isolate the $p54^{S6K}$ or $p85^{S6K}$ protein, respectively. Lysis and fractionation of $p54^{S6K}$ or $p85^{S6K}$ protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980) or other protein purification methods.

Polypeptides of the invention, particularly short $p54^{S6K}$ or $p85^{S6K}$ protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful $p54^{S6K}$ or $p85^{S6K}$ fragments or analogs.

Anti-$p54^{S6K}$ or $p85^{S6K}$ Antibodies

To generate $p54^{S6K}$ or $p85^{S6K}$ specific antibodies, a $p54^{S6K}$ or $p85^{S6K}$ coding sequence can be expressed as a C-terminal fusion with glutathione S-transferase (GST) (Smith et al., Gene 67:31–40, 1988). The fusion protein can be purified on glutathione-Sepharose beads, eluted with glutathione, cleaved with thrombin or another protease (at the engineered cleavage site), and purified to the degree necessary for immunization of rabbits. Primary immunizations can be carried out with Freund's complete adjuvant and subsequent immunizations with Freund's incomplete adjuvant. Antibody titers are monitored by Western blot and immunoprecipitation analyses, using the thrombin-cleaved $p54^{S6K}$ or $p85^{S6K}$ protein fragment of the GST-$p54^{S6K}$ or $p85^{S6K}$ fusion protein. Antisera are affinity purified using CNBr-Sepharose-coupled $p54^{S6K}$ or $p85^{S6K}$ protein or by other standard methods. Antiserum specificity is determined using a panel of unrelated GST proteins.

As an alternate or adjunct immunogen to GST fusion proteins, peptides corresponding to relatively unique regions of $p54^{S6K}$ or $p85^{S6K}$ may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using $p54^{S6K}$ or $p85^{S6K}$ expressed as a GST fusion protein.

Alternatively, monoclonal antibodies may be prepared using the $p54^{S6K}$ or $p85^{S6K}$ proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific $p54^{S6K}$ or $p85^{S6K}$ recognition by Western blot or immunoprecipitation analysis (by the methods described in Ausubel et al., supra). Antibodies which specifically recognize $p54^{S6K}$ or $p85^{S6K}$ are considered to be useful in the invention; such antibodies may be used, e.g., in an immunoassay to monitor the level of $p54^{S6K}$ or $p85^{S6K}$ produced by a mammal (for example, to determine the amount or subcellular location of $p54^{S6K}$ or $p85^{S6K}$).

Preferably, antibodies of the invention are produced using fragments of either the p54$^{S6K}$ or p85$^{S6K}$ proteins which lie outside regions highly conserved between p70$^{S6k}$, and p54$^{S6K}$ or p85$^{S6K}$, for example Ab#167, and appear likely to be antigenic, by criteria such as those provided by the Peptidestructure program of the Genetics Computer Group Sequence Analysis Package (Program Manual for the GCG Package, Version 7, 1991) using the algorithm of Jameson and Wolf (CABIOS 4:181 1988)). In one specific example, such fragments are generated by standard techniques of PCR and cloned into the pGEX expression vector (Ausubel et al., supra). Fusion proteins are expressed in E. coli and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Construction of a Non-human Transgenic Animal

Characterization of p54$^{S6K}$ or p85$^{S6K}$ can provide information that allows for the development of a p54$^{S6K}$ or p85$^{S6K}$ knockout mouse models by homologous recombination (or a p54$^{S6K}$ or p85$^{S6K}$ overproducing mouse, which may contain additional copies of the p54$^{S6K}$ or p85$^{S6K}$ gene, respectively, by other means of integration). The instant invention therefore also features a transgenic non-human animal containing a transgene which encodes a p54$^{S6K}$ or p85$^{S6K}$ polypeptide that is expressed in or delivered to tissue normally susceptible to unregulated proliferation.

A replacement type targeting vector can be constructed using an isogenic genomic clone from a mouse strain, e.g., 129/Sv (Stratagene La Jolla, Calif.). The targeting vector can be introduced into a J1 line of embryonic stem (ES) cells by electroporation to generate ES cell lines that carry a profoundly truncated form of a p54$^{S6K}$ or p85$^{S6K}$. To generate chimeric founder mice, the targeted cell lines will be injected into a mouse blastula stage embryo. Heterozygote offspring will be interbred to homozygosity. Knockout mice may be constructed as a means of screening in vivo for therapeutic compounds which modulate cell proliferation. Other non-human mammals such as rats, goats, or sheep may also be used for the expression of transgenic p54$^{S6K}$ or p85$^{S6K}$.

Cell lines that lack functional p54$^{S6K}$ or p85$^{S6K}$ or overexpress p54$^{S6K}$ or p85$^{S6K}$ are also a part of this invention.

Identification of Molecules that Modulate p54$^{S6K}$ or p85$^{S6K}$ Biological Activity Isolation of the p54$^{S6K}$ or p85$^{S6K}$ cDNA (as described herein) may also facilitate the identification of molecules which increase or decrease p54$^{S6K}$ or p85$^{S6K}$ biological activity. Similarly, molecules whose activity is modulated by p54$^{S6K}$ or p85$^{S6K}$ biological activity may also be identified. According to one approach, candidate molecules are added at varying concentrations to the culture medium of cells expressing p54$^{S6K}$ or p85$^{S6K}$ mRNA. p54$^{S6K}$ or p85$^{S6K}$ biological activity is then measured using standard techniques. The measurement of biological activity can include the measurement of p54$^{S6K}$ or p85$^{S6K}$ protein and nucleic acid levels, p54$^{S6K}$ or p85$^{S6K}$ phosphorylation, p54$^{S6K}$ or p85$^{S6K}$ kinase activity, or the effect of p54$^{S6K}$ or p85$^{S6K}$ on cell proliferation. Additionally, the measurement of biological activity can be done by using S6 or BRCA1 as substrates for p54$^{S6K}$ or p85$^{S6K}$ biological activity. For example, standard Northern blot analysis (Ausubel et al., supra) using a p54$^{S6K}$ or p85$^{S6K}$ cDNA (or cDNA fragment) as a hybridization probe can be used to measure levels of p54$^{S6K}$ or p85$^{S6K}$ expression, respectively. The level of p54$^{S6K}$ or p85$^{S6K}$ expression in the presence of the candidate molecule is compared to the level measured for the same cells in the same culture medium but in the absence of the candidate molecule.

If desired, the effect of candidate modulators on expression may, in the alternative, be measured at the level of p54$^{S6K}$ or p85$^{S6K}$ protein production using the same general approach and standard immunological detection techniques, such as Western blotting or immunoprecipitation with a p54$^{S6K}$ or p85$^{S6K}$-specific antibody (for example, the p54$^{S6K}$ antibody #167 described herein).

Candidate modulators may be purified (or substantially purified) molecules or may be one component of a mixture of compounds (e.g., an extract or supernatant obtained from cells; Ausubel et al., supra). In a mixed compound assay, p54$^{S6K}$ or p85$^{S6K}$ expression is tested against progressively smaller subsets of the candidate compound pool (e.g., produced by standard purification techniques, e.g., HPLC or FPLC) until a single compound or minimal compound mixture is demonstrated to modulate p54$^{S6K}$ or p85$^{S6K}$ expression, respectively.

Alternatively, or in addition, candidate compounds may be screened for those which modulate p54$^{S6K}$ or p85$^{S6K}$ cell proliferation inhibiting activity. In this approach, the degree of cell proliferation in the presence of a candidate compound is compared to the degree of cell proliferation in its absence, under equivalent conditions. Again, such a screen may begin with a pool of candidate compounds, from which one or more useful modulator compounds are isolated in a stepwise fashion. Cell proliferation activity may be measured by any standard assay, such as the mixed tumor transplantation (MTT) assay.

These assays may be done in a variety of ways that would be known to one of ordinary skill in the art. These include using p54$^{S6K}$ or p85$^{S6K}$ variants such as a kinase-dead mutant of p54$^{S6K}$ or p85$^{S6K}$, p54$^{S6K}$ KR or p85$^{S6K}$ KR; using fragments of p54$^{S6K}$ or p85$^{S6K}$, such as those described herein; or subjecting the cells to stimulation by the addition of serum or insulin, etc.

Test Compounds

Candidate p54$^{S6K}$ or p85$^{S6K}$ modulators include peptides, such as BRCA1, as well as non-peptide molecules (e.g., peptide or non-peptide molecules found, e.g., in a cell extract, mammalian serum, or growth medium on which mammalian cells have been cultured). In general, novel drugs for prevention or treatment of cellular proliferation are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for cell proliferation disorders should be employed whenever possible.

When a crude extract is found to regulate cellular proliferation, further fractionation of the positive lead extract is necessary to isolate chemical constituents responsible for the observed effect. Thus, the goal of the extraction, fractionation, and purification process is the careful characterization and identification of a chemical entity within the crude extract having cell proliferation, -preventative, or -palliative activities. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using a mammalian cell proliferation model.

Modulators found to be effective at the level of $p54^{S6K}$ or $p85^{S6K}$ expression or activity may be confirmed as useful in animal models and, if successful, may be used as anti-cancer therapeutics for either the inhibition or the enhancement of cell proliferation, as appropriate.

Diagnosis of a Condition Involving Altered Cell Proliferation $p54^{S6K}$ or $p85^{S6K}$ polypeptides and nucleic acid sequences may find diagnostic use in the detection or monitoring of conditions involving aberrant levels of cell proliferation. For example, altered expression of $p54^{S6K}$ or $p85^{S6K}$ may be correlated with enhanced cell proliferation in humans. Accordingly, a decrease or increase in the level of $p54^{S6K}$ or $p85^{S6K}$ production may provide an indication of a deleterious condition. Levels of expression may be assayed by any standard technique. For example, $p54^{S6K}$ or $p85^{S6K}$ expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY; and Yap and McGee, Nucl. Acids. Res. 19:4294, 1991).

Alternatively, a patient sample may be analyzed for one or more mutations in the $p54^{S6K}$ or $p85^{S6K}$ sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant $p54^{S6K}$ or $p85^{S6K}$ detection, and each is well known in the art; examples of particular techniques are described, without limitation, in Orita et al. (Proc. Natl. Acad. Sci. USA 86:2766–2770, 1989); and Sheffield et al.(Proc. Natl. Acad. Sci. USA 86:232–236, 1989).

In yet another approach, immunoassays are used to detect or monitor $p54^{S6K}$ or $p85^{S6K}$ proteins in a biological sample. $p54^{S6K}$ or $p85^{S6K}$ specific polyclonal or monoclonal antibodies (produced as described above) may be used in any standard immunoassay format (e.g., ELISA, Western blot, or RIA assay) to measure $p54^{S6K}$ or $p85^{S6K}$ polypeptide levels; again comparison is to wild-type $p54^{S6K}$ or $p85^{S6K}$ levels, respectively, and an alteration in $p54^{S6K}$ or $p85^{S6K}$ production is indicative of a condition involving increased cell proliferation. Examples of immunoassays are described, e.g., in Ausubel et al., supra. Immunohistochemical techniques may also be utilized for detection. For example, a tissue sample may be obtained from a patient, and a section stained for the presence of $p54^{S6K}$ or $p8_5^{S6K}$ using an anti-$p54^{S6K}$ or $p85^{S6K}$ antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of protein production, for example, by immunological techniques or the protein truncation test (Hogerrorst, F. B. L., et al., Nature Genetics 10:208–212, 1995) and also includes a nucleic acid-based detection technique designed to identify more subtle mutations (for example, point mutations). As described above, a number of mismatch detection assays are available to those skilled in the art, and any preferred technique may be used (see above). By this approach, mutations in $p54^{S6K}$ or $p85^{S6K}$ may be detected that either result in loss of $p54^{S6K}$ or $p85^{S6K}$ expression or loss of $p54^{S6K}$ or $p85^{S6K}$ biological activity, respectively. In a variation of this combined diagnostic method, biological activity is measured as protease activity using any appropriate protease assay system (for example, those described above).

Mismatch detection assays also provide the opportunity to diagnose a mediated predisposition to diseases of cell proliferation. For example, a patient heterozygous for a $p54^{S6K}$ or $p85^{S6K}$ mutation may show no clinical symptoms and yet possess a higher than normal probability of developing one or more types of cancer or cell proliferative diseases. Given this diagnosis, a patient may take precautions to minimize their exposure to adverse environmental factors (for example, UV exposure or chemical mutagens) and to carefully monitor their medical condition (for example, through frequent physical examinations). This type of diagnostic approach may also be used to detect mutations in prenatal screens.

The diagnostic assays described above may be carried out using any biological sample (for example, any biopsy sample or bodily fluid or tissue) in which $p54^{S6K}$ or $p85^{S6K}$ is normally expressed (for example, the inhibition of cell proliferation). Identification of a mutant $p54^{S6K}$ or $p85^{S6K}$ gene may also be assayed using these sources for test samples. Alternatively, a $p54^{S6K}$ or $p85^{S6K}$ mutation, particularly as part of a diagnosis for predisposition to $p54^{S6K}$ or $p85^{S6K}$-associated proliferative disease, may be tested using a DNA sample from any cell, for example, by mismatch detection techniques; preferably, the DNA sample is subjected to PCR amplification prior to analysis.

$p54^{S6K}$ or $p85^{S6K}$ Therapy

Because expression levels of $p54^{S6K}$ or $p85^{S6K}$ genes may correlate with the levels of cell proliferation, the $p54^{S6K}$ or $p85^{S6K}$ gene can also be used in anti-cell proliferation gene therapy. In particular, to inhibit neoplastic cells, either a functional or a dominant-negative $p54^{S6K}$ or $p85^{S6K}$ gene may be introduced into cells at the sites predicted to undergo undesirable cell proliferation.

Retroviral vectors, adenoviral vectors, adeno-associated viral vectors, or other viral vectors with the appropriate tropism for cells likely to be involved in cell proliferation may be used as a gene transfer delivery system for a therapeutic $p54^{S6K}$ or $p85^{S6K}$ gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into cells otherwise predicted to undergo cell proliferation. For example, $p54^{S6K}$ or $p85^{S6K}$ may be introduced into a neoplastic cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic $p54^{S6K}$ or $p85^{S6K}$ DNA construct is preferably applied to the site of the predicted cell proliferation event (for example, by injection), but may also be applied to tissue in the vicinity of the predicted cell proliferation event or even to a blood vessel supplying the cells predicted to undergo cell proliferation.

In the gene therapy constructs, $p54^{S6K}$ or $p85^{S6K}$ cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in neural cells or T-cells may be used to direct $p54^{S6K}$ or $p85^{S6K}$ expression. Such enhancers include, without limitation, those enhancers which are characterized as tissue or cell specific in their expression.

Alternatively, if a $p54^{S6K}$ or $p85^{S6K}$ genomic clone is utilized as a therapeutic construct (for example, following its isolation by hybridization with the $p54^{S6K}$ or $p85^{S6K}$ cDNA), $p54^{S6K}$ or $p85^{S6K}$ expression is regulated by its cognate regulatory sequences or, if desired, by regulatory sequences derived from a heterologous source, e.g., any of the promoters or regulatory elements described above.

Less preferably, $p54^{S6K}$ or $p85^{S6K}$ gene therapy is accomplished by direct administration of the $p54^{S6K}$ or $p85^{S6K}$ mRNA to a cell predicted to undergo cell proliferation. This mRNA may be produced and isolated by any standard technique, but is most readily produced by in vitro transcription using a $p54^{S6K}$ or $p85^{S6K}$ cDNA under the control of a high efficiency promoter (e.g., the T7 promoter). Administration of $p54^{S6K}$ or $p85^{S6K}$ mRNA to malignant cells is carried out by any of the methods for direct nucleic acid administration described above.

Ideally, the production of $p54^{S6K}$ or $p85^{S6K}$ proteins by any gene therapy approach described above results in a cellular level of $p54^{S6K}$ or $p85^{S6K}$, respectively, that is at least equivalent to the normal, cellular level of $p54^{S6K}$ or $p85^{S6K}$ in an unaffected individual. Treatment by any $p54^{S6K}$ or $p85^{S6K}$-mediated gene therapy approach may be combined with more traditional therapies.

Another therapeutic approach included within the invention involves direct administration of recombinant $p54^{S6K}$ or $p85^{S6K}$ proteins, either to the site of a predicted cell proliferation event (for example, by injection) or systemically by any conventional recombinant protein administration technique. The actual dosage of $p54^{S6K}$ or $p85^{S6K}$ depends on a number of factors, including the size and health of the individual patient, but, generally, between 0.1 mg and 100 mg inclusive are administered per day to an adult in any pharmaceutically-acceptable formulation.

In a patient diagnosed to be heterozygous for a $p54^{S6K}$ or $p85^{S6K}$ mutation or to be susceptible to $p54^{S6K}$ or $p85^{S6K}$ mutations (even if those mutations do not yet result in alteration or loss of biological activity), or a patient diagnosed as HIV positive, any of the above therapies may be administered before the occurrence of the disease phenotype. For example, the therapies may be provided to a patient who is HIV positive but does not yet show a diminished T-cell count or other signs of full-blown AIDS. In particular, compounds shown to increase expression or biological activity may be administered by any standard dosage and route of administration (see above). Alternatively, gene therapy using a $p54^{S6K}$ or $p85^{S6K}$ expression construct may be undertaken to reverse or prevent the cell defect prior to the development of the proliferative disease.

The methods of the instant invention may be used to reduce or diagnose the disorders described herein in any mammal, for example, humans, domestic pets, or livestock. Where a non-human mammal is treated or diagnosed, the polypeptide, nucleic acid, or antibody employed is preferably specific for that species.

Administration of $p54^{S6K}$ or $p85^{S6K}$ Polypeptides, $p54^{S6K}$ or $p85^{S6K}$ Genes, or Modulators of Synthesis or Function A $p54^{S6K}$ or $p85^{S6K}$ protein, gene, or modulator may be administered with a pharmaceutically-acceptable diluent, carrier, or excipient, in unit dosage form. Conventional pharmaceutical practice may be employed to provide suitable formulations or compositions to administer $p54^{S6K}$ or $p85^{S6K}$ to patients suffering from or presymptomatic for a $p54^{S6K}$ or $p85^{S6K}$-associated cell proliferative disease. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a p54$^{S6K}$ or p85$^{S6K}$ protein, gene, or modulatory compound may be combined with more traditional therapies for the disease such as, for example, surgery, radiation, or chemotherapy for cancers; surgery, steroid therapy, and chemotherapy for autoimmune diseases; antiviral therapies for AIDS; and antibiotics for opportunistic infections.

The following examples are to illustrate the invention. They are not meant to limit the invention in any way.

EXAMPLE 1

Cloning of the p54$^{S6K}$ Gene

Our search for human genes potentially involved in cellular proliferation resulted in the identification of a clone, isolated from human brain, in the expressed sequence tag (EST) database. This clone had extensive but dispersed homology to p70$^{S6k}$, a serine/threonine kinase involved in cellular proliferation.

Using the EST sequence information we probed a human Jurkat T cell lambda cDNA library (Stratagene) and obtained eight clones, two of which contained complete open reading frames. Sequencing of the two clones showed they were identical. We have named the clone p54$^{S6K}$. FIG. 1A shows the DNA and amino acid sequences of of p54$^{S6K}$. Multiple sequencing of the of clones isolated from the library as well as the examination of p54$^{S6K}$ EST clones show that seven of the clones have T at the nucleotide position 1294 (encoding valine at amino acid position 420), whereas four contain C at the position 1294 (encoding alanine at 420). Three clones isolated from the Jurkat library (including the two full-length clones) have A at the nucleotide position at 1203 (encoding methionine at amino acid position 390), whereas one partial clone isolated from the Jurkat library, as well as four EST entries, had G at the nucleotide position at 1203 (encoding valine at amino acid position 390).

The p54$^{S6K}$ cDNA clones, as well as oligonucleotides derived from the cDNA sequence, together with available genomic DNA libraries can be used to further delineate the structure and genomic organization of p54$^{S6K}$. Strategies for this are well known in the art and may include sequencing, restriction mapping, Southern blot analysis and inverse PCR techniques. These techniques may also be used to map homologs and additional genes.

EXAMPLE 2

Northern Blot Analysis of the p54$^{S6K}$ Transcript

Figure 2:
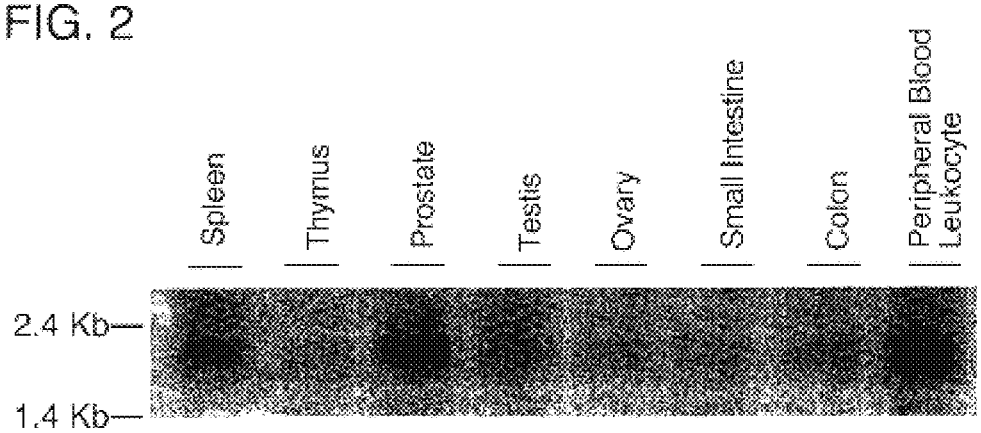
FIG. 2 shows an image of a Northern blot of p54$^{S6K}$. Poly(A)+ mRNAs from multiple human tissues, probed with a 0.7 kb fragment of p54$^{S6K}$ cDNA labeled with [α-$^{32}$P] dCTP. The RNA size markers are shown on the left.

A human multiple tissue northern (MTN II, Clontech, Palo Alto, Calif.) was probed with a 32P-labeled 0.7 kb fragment of p54$^{S6K}$ using Clontech protocols (Clontech). FIG. 2 shows the Northern Blot analysis of p54$^{S6K}$ using a human multiple tissue poly(A)+ mRNA blot. p54$^{S6K}$ does not have alternatively-spliced variants; only one mRNA species of approximately 1.9 kb is detected. Northern blot analysis of mRNA isolated from the Jurkat cell line also shows one transcript of approximately 1.9 kb. Multiple tissue northern shows that p54$^{S6K}$ is ubiquitously expressed, with a higher level of expression in prostate, spleen, and peripheral blood leukocytes. Although we had isolated p54$^{S6K}$ based on the sequence of one EST clone, several more EST clones have been posted since the cloning of p54$^{S6K}$. Some of these ESTs were isolated from various tissues such as brain, colon, and parathyroid gland, and in transformed tissues such as colon tumor, breast tumor, and Wilms' tumor.

EXAMPLE 3

Characterization of p54$^{S6K}$ Protein

The predicted molecular weight of p54$^{S6K}$ is 53.5 kDa, and in vitro transcription/translation of the two full-length clones of p54$^{S6K}$ shows that the apparent molecular weight of the protein in SDS-PAGE is 54 kDa. The molecular weight of p54$^{S6K}$ was also verified using an antiserum generated, using standard techniques, against a C-terminal peptide (FIG. 3A).

Figure 3A:
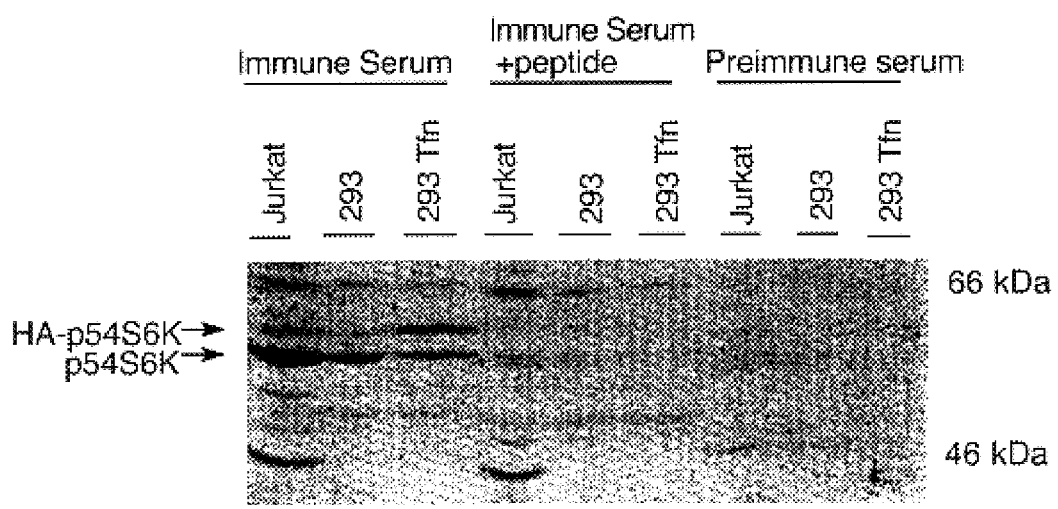
FIG. 3A shows an image of a Western blot of lysates from human Jurkat T cells, 293 cells, and 293 cells transiently transfected with HA-p54$^{S6K}$ and immunoblotted with Ab#167, Ab#167 incubated with the immunizing peptide, and the preimmune sera. Arrows on the left show the bands corresponding to the indicated proteins. The protein size markers are shown on the right.

Antibody (Ab.) #167, raised against a peptide containing a C-terminal sequence of p54$^{S6K}$, distinct from p70$^{S6k}$, immunoblotted a 54 kDa protein in the lysates of Jurkat cells and HEK 293 cells (FIG. 3A). Lysates from the 293 cells transfected with hemagglutinin (HA)-tagged p54$^{S6K}$ showed the endogenous protein at 54 kDa as well as the 56 kDa tagged protein. Immunoblotting with the preimmune serum or with the antiserum incubated with the immunizing peptide showed that the antisera was specific to the 54 kDa band (FIG. 3A).

Amino acid sequence comparison between p54$^{S6K}$ and p70$^{S6k}$ shows extensive homology (FIG. 1B). The catalytic domain is most similar with amino acid sequence homology of 84%, whereas the N-terminal and C-terminal domains are 43% and 59% homologous, respectively. The acidic region found on the N-terminus of p70$^{S6k}$, which is thought to be important for interaction with the basic pseudosubstrate domain for kinase activity inhibition, is also found in p54$^{S6K}$. Many amino acid residues in p70$^{S6k}$ that have been shown to be important for its regulation are also conserved on p54$^{S6K}$. With the exception of T421, the proline-directed phosphorylation sites in the C-terminal pseudosubstrate domain of p70$^{S6k}$, S404, S411, and S424, are conserved. The recently identified S371, which is important for the function of p70$^{S6k}$, is also conserved on p54$^{S6K}$. T229, S411, T389, and S404, the p70$^{S6k}$ residues whose phosphorylation was shown to be regulated downstream of mTOR and PI 3-kinase, are conserved.

EXAMPLE 4

Activation of p54$^{S6K}$ Kinase Activity

We studied the regulation of p54$^{S6K}$ activity by using both transient transfection of epitope-tagged proteins as well as antibodies raised against the endogenous protein.

For transient transfections HEK 293 cells were cultured in standard (DMEM complete) media and transfected with the indicated DNA using a CaPO$_4$ precipitation method. Alternative methods of transfection, such as by electroporation, DEAE-Dextran treatment, or mediated by liposomes, may also be used. The experiments may also be done using cell lines, created by stable transfection techniques and expressing various forms of p54$^{S6K}$.

Antibodies were made using standard techniques, such as those described in Harlow and Lane (Antibodies: A Laboratory Manual, Cold Spring Harbor Press, New York. 1988). The cells were starved and then stimulated with serum, EGF, or insulin, or left unstimulated. Rapamycin or wortmannin were also incubated with the cells prior to serum stimulation when indicated.

Figure 3B:
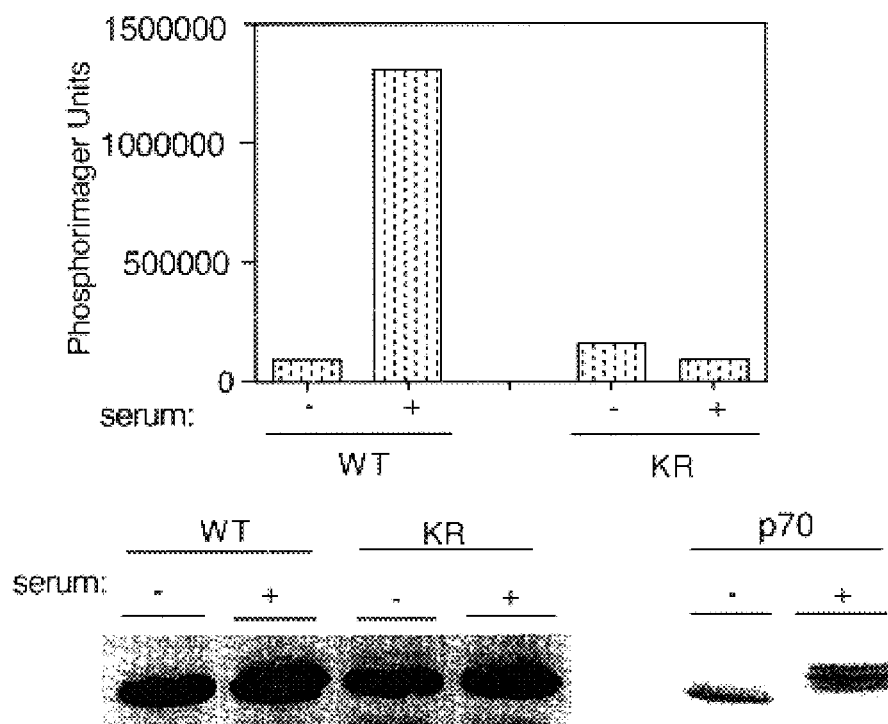
FIG. 3B shows a graphical representation of the intrinsic kinase activity of p54$^{S6K}$. p54$^{S6K}$ does not undergo an electrophoretic mobility shift upon serum stimulation. HA-p54$^{S6K}$ or HA-p54$^{S6K}$ KR were transfected into 293 cells, stimulated with serum, and the lysates were immunoprecipitated with anti-HA Ab. In vitro kinase assay of the anti-HA Ab immunoprecipitates using GST-S6 as the substrate is shown as a graph. A portion of the lysates were immunoblotted with anti-HA Ab to show the expression level of HA-p54$^{S6K}$ and HA-p54$^{S6K}$ KR as well as their lack of mobility shift upon serum stimulation (bottom left panel). The bottom right panel shows an image of an endogenous p70$^{S6k}$ immunoblot of lysates from quiescent or stimulated 293 cells in order to show the electrophoretic mobility shift of p70$^{S6K}$ upon serum stimulation.
Figure 3C:
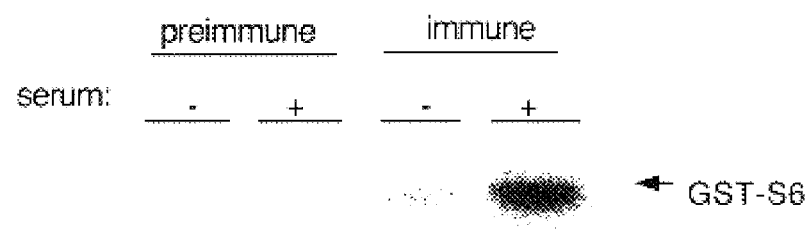
FIG. 3C shows an image of Western blot of endogenous p54$^{S6K}$ kinase activity. 293 cells were treated with serum for 20 minutes, lysed, and the lysates were immunoprecipitated with 167 immune or preimmune serum. In vitro kinase assay of the immunoprecipitates using GST-S6 as the substrate is shown.
Figure 3D:
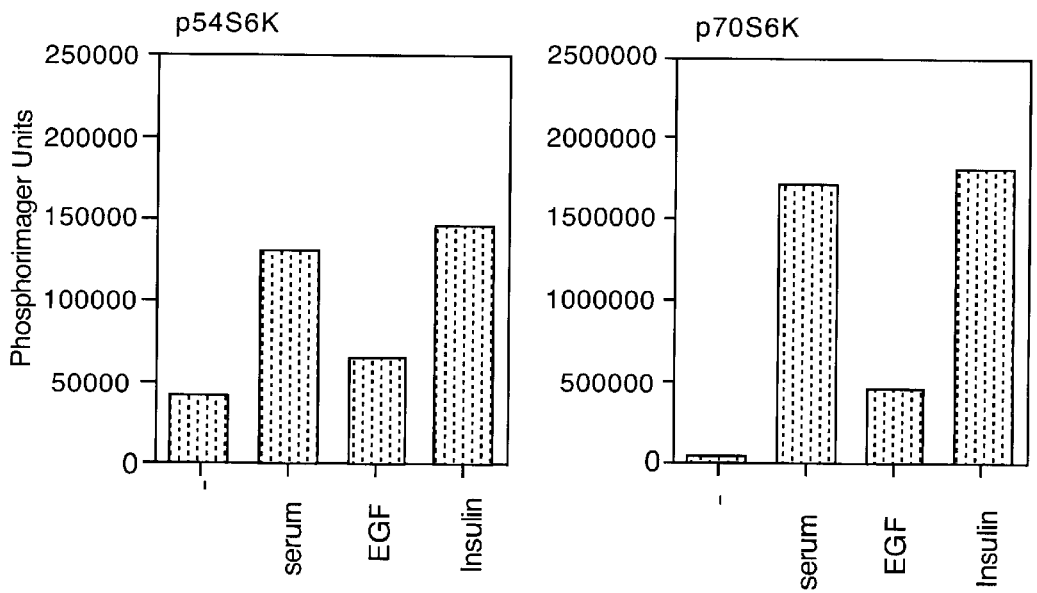
FIG. 3D shows a graph demonstrating that p54$^{S6K}$ kinase activity is stimulated by serum and insulin, and to some extent by EGF. 293 cells were treated with serum (10%), EGF (250 ng/ml), or insulin (200 nM) for 20 minutes, lysed, and the lysates were immunoprecipitated with 167 anti-p54$^{S6K}$ antiserum or with N2 anti-p70$^{S6k}$ antiserum. Phosphorimager™ counts from an in vitro kinase assay of the immunoprecipitates using GST-S6 as the substrate are shown.
Figure 3E:
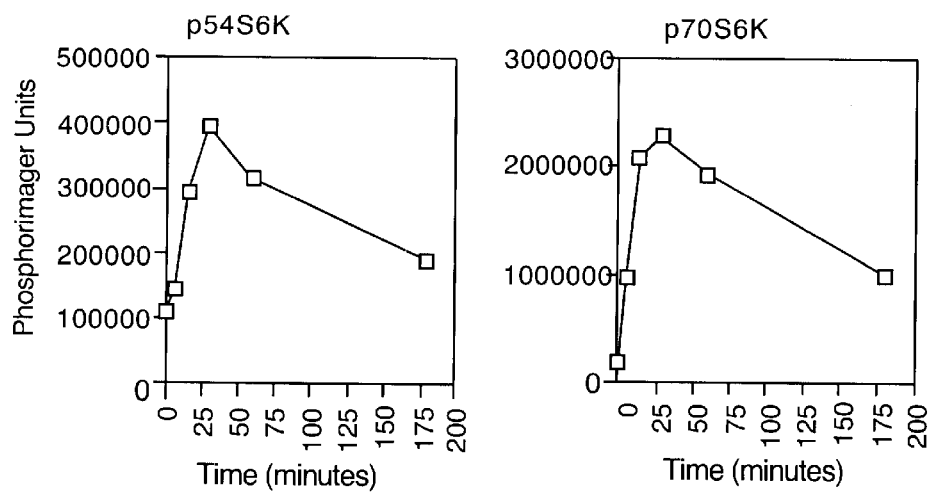
FIG. 3E is a graphical illustration of the maximal activation of p54$^{S6K}$ and p70$^{S6k}$, which occurs at 30 minutes. 293 cells were treated with serum (10%) for 0, 5, 15, 30, 60, and 180 minutes, lysed, and the lysates were immunoprecipitated with either 167 anti-p54$^{S6K}$ antiserum or with N2 anti-p70$^{S6k}$ antiserum. Phosphorimager counts from an in vitro kinase assay of the immunoprecipitates using GST-S6 as the substrate are shown.

A p54$^{S6K}$ mutant was generated by changing the catalytic lysine to arginine at position 99. This mutant was called p54$^{S6K}$ KR. HEK 293 cells were transfected with the DNA for HA-tagged p54$^{S6K}$ or p54$^{S6K}$ KR, stimulated with serum, and the proteins were immunoprecipitated from cell lysates for an in vitro kinase assay, using standard techniques. Glutathione-S-transferase (GST)-tagged S6 was used as a substrate since screening of different substrates in an in vitro kinase assay showed that p54$^{S6K}$ can phosphorylate both S6 and histone H2B. The graph in FIG. 3B shows that p54$^{S6K}$ kinase activity towards S6 was stimulated by serum treatment of the cells. The KR mutation of p54$^{S6K}$ abolished the kinase activity in an in vitro kinase assay, indicating that the kinase activity belongs to p54$^{S6K}$ itself and not to an associated kinase(s). Serum also increased the activity of endogenous p54$^{S6K}$ when endogenous p54$^{S6K}$ was immunoprecipitated using 167 antiserum and an in vitro kinase assay was carried out (FIG. 3C).

p54$^{S6K}$ does not undergo a dramatic electrophoretic mobility shift on SDS-PAGE when it becomes phosphorylated upon stimulation (FIG. 3B). Lysates from 293 cells transfected with HA-p54$^{S6K}$ or HA-p54$^{S6K}$ KR were immunoblotted with anti-HA Ab. (FIG. 3B bottom left panel). The immunoblots show no mobility shift for p54$^{S6K}$ upon serum stimulation, whereas p70$^{S6k}$ shows a distinct shift (FIG. 3B bottom right panel). This is of interest since a majority of the p70$^{S6k}$ phosphorylation sites are conserved in p54$^{S6K}$ (FIG. 1B). HEK 293 cells were also treated with various mitogens and p54$^{S6K}$ activity assessed. p54$^{S6K}$ was stimulated by serum and insulin, and to a small degree by EGF in 293 cells (FIG. 3D). Similarly, p70$^{S6k}$ was strongly activated by serum and insulin but only mildly activated by EGF. Finally, the activation kinetics of p54$^{S6K}$ and p70$^{S6k}$ were compared. FIG. 3E shows that both kinases were maximally activated by 30 minutes following stimulation by serum.

EXAMPLE 5

Regulation of p54$^{S6K}$ Activity

Figure 4A:
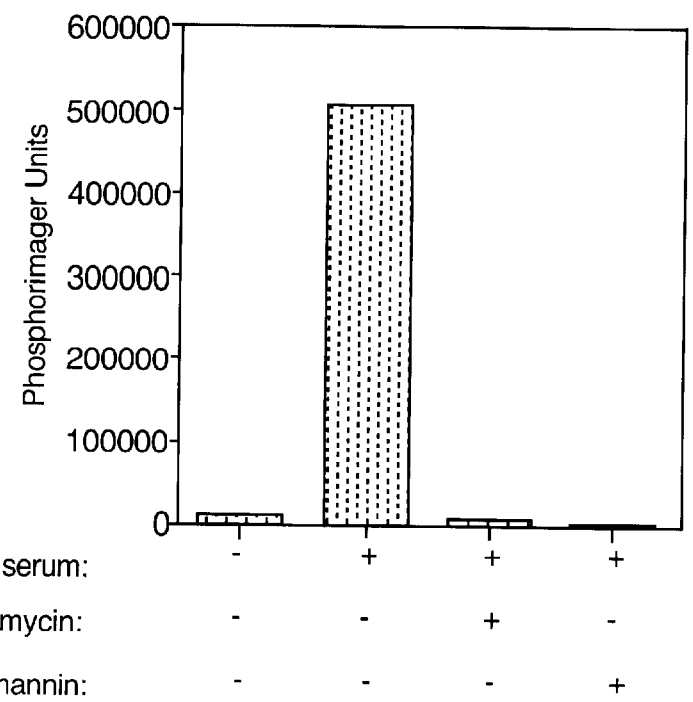
FIG. 4A is a graph demonstrating that rapamycin and wortmannin inhibit p54$^{S6K}$ kinase activity. 293 cells transfected with HA-p54$^{S6K}$ were treated with rapamycin (20 ng/ml) or wortmannin (100 nM) for 20 minutes prior to serum stimulation (10%, 20 minutes). The cells were lysed, and the lysates were immunoprecipitated with anti-HA Ab. Phosphorimager counts from an in vitro kinase assay of the immunoprecipitates using GST-S6 as the substrate are shown.
Figure 4B:
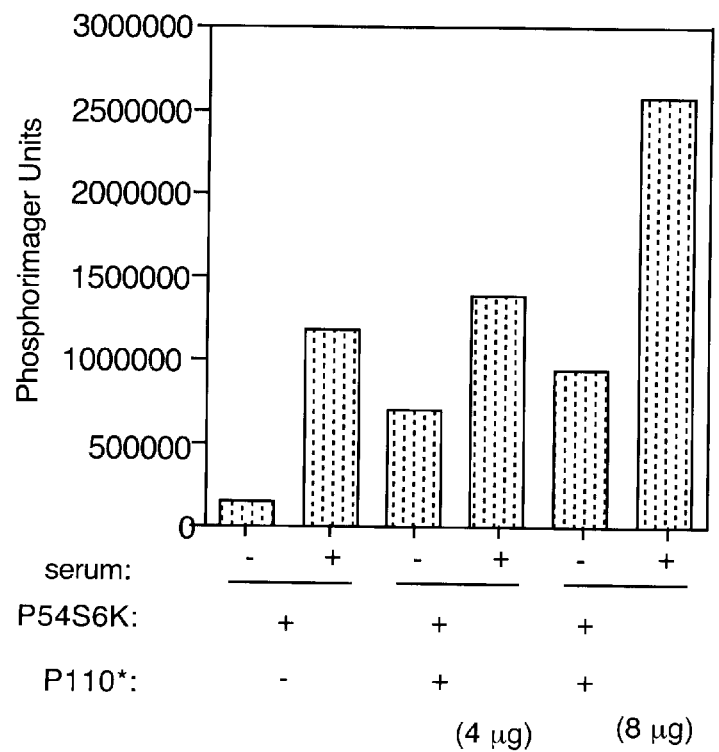
FIG. 4B is a graph showing that p110* increases both the basal and serum-stimulated activity of p54$^{S6K}$. 293 cells were transfected with the DNA for p54$^{S6K}$ alone or for p54$^{S6K}$ and two different amounts of p110* DNA as indicated. Equal expression of proteins was verified by immunoblots. The cells were stimulated with serum (10%, 20 minutes), lysed, and the lysates were immunoprecipitated with anti-HA Ab. Phosphorimager™ counts from an in vitro kinase assay of the immunoprecipitates using GST-S6 as the substrate are shown.

In order to assess the signaling pathways involved in regulating p54$^{S6K}$ activity, pharmacological agents and mutant forms of various signaling proteins were used. Increase in p54$^{S6K}$ kinase activity by serum was inhibited by rapamycin and wortmannin (FIG. 4A), suggesting that both P13-kinase and mTOR regulate p54$^{S6K}$ kinase activation. When 293 cells were transiently transfected with p54$^{S6K}$ and p110*, an active form of the p110 catalytic subunit of PI 3-kinase, the basal as well as the serum-stimulated p54$^{S6K}$ kinase activity was increased (FIG. 4B). This is similar to p70$^{S6k}$ activity regulation in that active p110, when co-transfected with p70$^{S6k}$, enhances p70$^{S6k}$ activity.

Figure 4C:
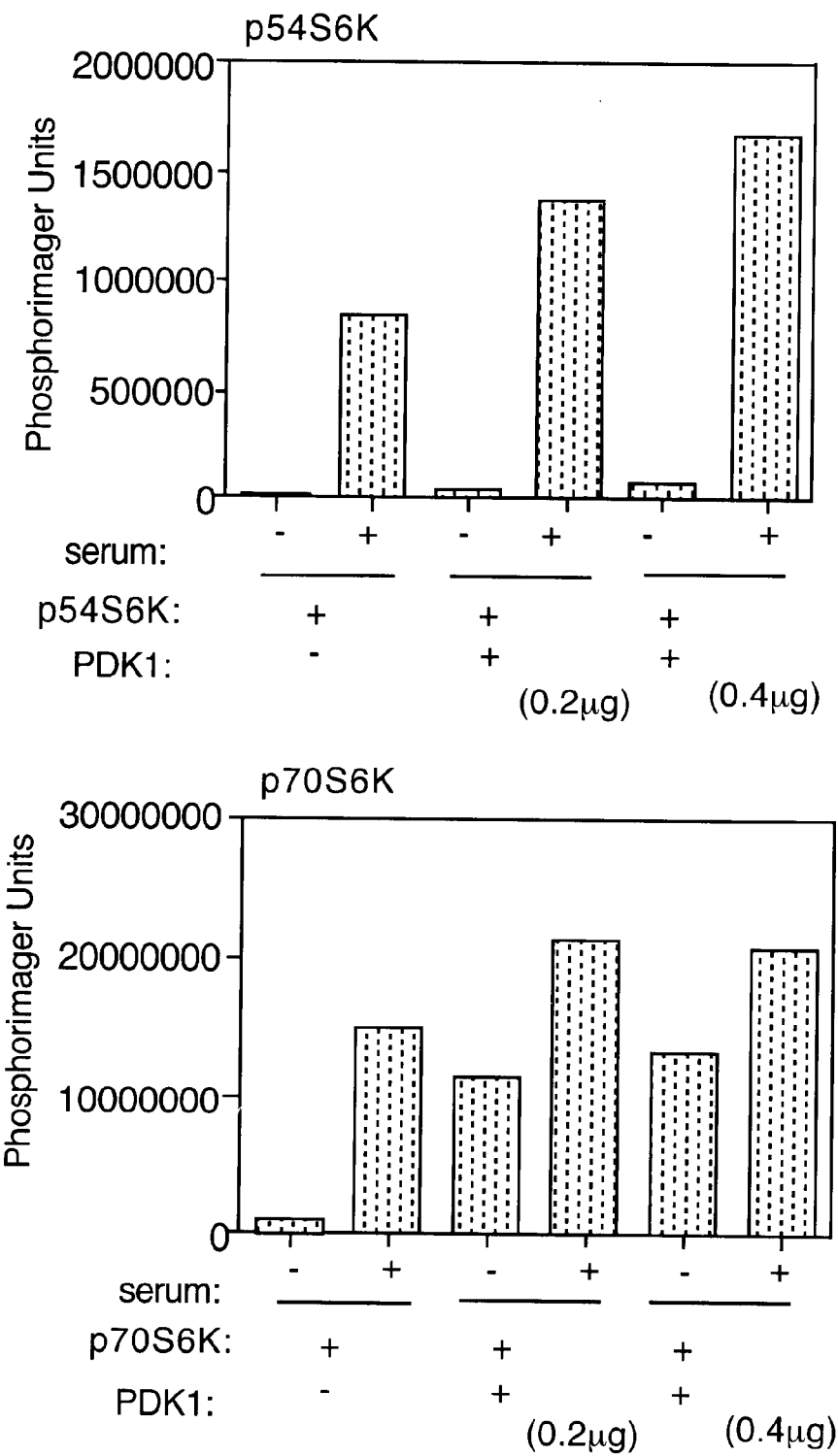
FIG. 4C is a graph illustrating that the kinase activities of p54$^{S6K}$ and p70$^{S6k}$ are differentially regulated by PDK1. 293 cells were transfected with DNA for p54$^{S6K}$ alone; for p54$^{S6K}$ alone; for p54$^{S6K}$ and two different concentrations of DNA for PDK1 (top panel); or for p70$^{S6k}$ and two different concentrations of DNA for PDK1 as indicated (bottom graph). Equal expression of the proteins was verified by immunoblots. The cells were stimulated with serum, lysed, and the lysates were immunoprecipitated with anti-HA Ab. Phosphorimager counts from an in vitro kinase assay of the immunoprecipitates using GST-S6 as the substrate are shown.

It has recently been shown that PDK1 is a direct upstream activator of p70$^{S6k}$. PDK1 is a serine-threonine kinase that contains a pleckstrin homology domain. It phosphorylates Akt/PKB at S308 in the activation loop, and it has been shown to phosphorylate the equivalent site T229 on p70$^{S6k}$. The role of PDK1 in p54$^{S6K}$ activation was assessed. Co-transfection of PDK1 and p70$^{S6k}$ showed that PDK1 enhances the basal activity of p70$^{S6k}$ as well as the serum-stimulated kinase activity of p70$^{S6k}$ (FIG. 4C). At the same level of expression that enhances p70$^{S6k}$ activity, PDK1 failed to enhance the basal activity level of p54$^{S6K}$. However, the presence of PDK1 enhanced the serum-stimulated p54$^{S6K}$ activity level. Therefore overexpression of PDK1 alone without further stimulation by serum is sufficient to activate p70$^{S6k}$ but not p54$^{S6K}$.

EXAMPLE 6

The p85$^{S6K}$ Polypeptide

An alternative splice variant of the gene encoding p54$^{S6K}$ has also been discovered. This alternative splicing event results in the translation of a polypeptide homologous to p70$^{S6K}$ and p54$^{S6K}$, called p85$^{S6K}$. This polypeptide has a molecular weight of approximately 85 kDa.

DESCRIPTION OF THE PREFERRED EMBODIMENTS

In other embodiments, the invention includes any protein which is substantially identical to the p54$^{S6K}$ or p85$^{S6K}$ polypeptides shown in FIGS. 1 or 5; such homologs include other substantially pure naturally-occurring mammalian proteins as well as allelic variants; natural mutants; induced mutants; DNA sequences which encode p54$^{S6K}$ or p85$^{S6K}$ proteins and also hybridize to p54$^{S6K}$ or p85$^{S6K}$ DNA sequences under high stringency conditions or, less preferably, under low stringency conditions (e.g., washing at 2X SSC at 40° C. with a probe length of at least 40 nucleotides); and proteins specifically bound by antisera directed to a p54$^{S6K}$ or p85$^{S6K}$ polypeptide. The term also includes chimeric polypeptides that include a portion of a p54$^{S6K}$ or p85$^{S6K}$ polypeptide.

The invention further includes analogs of any of the naturally-occurring polypeptides described herein. Analogs can differ from the naturally-occurring protein by amino acid sequence differences, by post-translational modifications, or by both. Analogs of the invention will generally exhibit at least 85%, more preferably 90%, and most preferably 95% or even 99% identity with all or part of a naturally-occurring amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, supra, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a p54$^{S6K}$ or p85$^{S6K}$ nucleic acid or amino acid sequence in a sample to be diagnosed.

All publications mentioned in this specification are herein incorporated by reference to the same extent as if each independent publication or patent application was specifically and individually indicated to be incorporated by reference.

What is claimed is:

1. A substantially pure p54$^{S6K}$ polypeptide with kinase activity, wherein said p54$^{S6K}$ polypeptide has at least 99% amino acid sequence identity to SEQ ID NO: 3.

2. A substantially pure p85$^{S6K}$ polypeptide with kinase activity, wherein said p85$^{S6K}$ polypeptide has at least 99% amino acid sequence identity to SEQ ID NO: 4.

3. A substantially pure p54$^{S6K}$ polypeptide with SEQ ID NO: 3 wherein the amino acid at position 99 is changed from lysine to arginine, or is a fusion with a heterologous polypeptide, or has a post-translational modification.

4. A substantially pure p85$^{S6K}$ polypeptide with kinase activity, wherein said p85$^{S6K}$ polypeptide fragment has at least 99% amino acid sequence identity to SEQ ID NO: 4, and wherein said polypeptide is a fusion with a heterologous polypeptide, or has a post-translational modification.

5. The substantially pure p54$^{S6K}$ polypeptide of SEQ ID NO: 3.

6. The substantially pure p85$^{S6K}$ polypeptide of SEQ ID NO: 4.

7. The substantially pure p54$^{S6K}$ polypeptide of claim 5, wherein the amino acid at position 420 of SEQ ID NO: 3 is changed from valine to alanine.

8. The substantially pure p54$^{S6K}$ polypeptide of claim 5, wherein the amino acid at position 390 of SEQ ID NO: 3 is changed from methionine to valine.

9. The substantially pure p54$^{S6K}$ polypeptide of claim 5, wherein said polypeptide has kinase activity.

10. The substantially pure p85$^{S6K}$ polypeptide of claim 6, wherein said polypeptide has kinase activity.

* * * * *

UNITED STATES PATENT AND TRADEMARK OFFICE
CERTIFICATE OF CORRECTION

PATENT NO.    : 6,372,467 B1
DATED         : April 16, 2002
INVENTOR(S)   : John Blenis, Kay K. Lee-Fruman and Calvin J. Kuo It is certified that error appears in the above-identified patent and that said Letters Patent is hereby corrected as shown below:

Column 1,
Line 14, after "funding" insert -- (NIH Grant GM51405)--;
Line 48, replace "$^{or\ p}85^{S6K}$" with -- or $p85^{S6K}$ --;
Line 56, replace "4-10" with -- 4-9 --;
Line 63, replace "NOs: 1 or 2" with -- NO:1 --;

Column 2,
Line 3, replace "modification" with -- modification. --;
Line 21, replace "$p85^{S6K}$" with -- $p85^{S6K}$ --;

Column 6,
Line 16, replace "f" with -- of --;

Column 7,
Line 22, replace "f" with -- of --;
Line 67, replace "$p70^{S6K}$" with -- $p70^{S6k}$ --;

Column 11,
Line 54, replace "$p54^{56}K$" with -- $p54^{S6K}$ --;

Column 14,
Line 10, replace "$p85^{S6K}$ specific" with -- $p85^{S6K}$_ specific --;
Line 20, replace "$p8_5^{S6K}$" with -- $p85^{S6K}$ --;

Column 15,
Line 19, replace "15-14" with -- 1:5-14 --;

Column 16,
Line 35, replace "patent" with -- patient --;

UNITED STATES PATENT AND TRADEMARK OFFICE
CERTIFICATE OF CORRECTION

PATENT NO.    : 6,372,467 B1
DATED         : April 16, 2002
INVENTOR(S)   : John Blenis, Kay K. Lee-Fruman and Calvin J. Kuo It is certified that error appears in the above-identified patent and that said Letters Patent is hereby corrected as shown below:

Column 17,
Line 50, replace "of of p54$^{S6K}$" with -- of p54$^{S6K}$ -- ;
Line 51, replace "of the of" with --of the --; and Column 20,
Line 23, replace "p85$^{S6K}$" with -- p85$^{S6K}$. --.

Signed and Sealed this

Eleventh Day of February, 2003

JAMES E. ROGAN
*Director of the United States Patent and Trademark Office*

Adverse Decisions in Interference

Patent No. 6,372,467, John Blenis, Kay K. Lee-Fruman and Calvin J. Kuo, P54S6K AND P85S6K GENES, PROTEINS, PRIMERS, PROBES, AND DETECTION METHODS, Interference No. 105,722, final judgment adverse to the patentees rendered December 3, 2009, as to claims 1, 3, 5, and 9.

*(Official Gazette, July 27, 2010)*

UNITED STATES PATENT AND TRADEMARK OFFICE
CERTIFICATE OF CORRECTION

| | |
|---|---|
| PATENT NO. | : 6,372,467 B1 |
| APPLICATION NO. | : 09/430564 |
| DATED | : April 16, 2002 |
| INVENTOR(S) | : John Blenis et al. |

It is certified that error appears in the above-identified patent and that said Letters Patent is hereby corrected as shown below:

In the Specification

Column 1, Line 13 replace:
"This invention was made in part with Government funding, and the Government therefore has certain rights in the invention."

With:
--This invention was made with government support under GM051405 awarded by National Institutes of Health (NIH). The government has certain rights in this invention.--

Signed and Sealed this
Seventh Day of March, 2023

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 1732
<212> TYPE: DNA
<213> ORGANISM: Homo sapiens

<400> SEQUENCE: 1

| | | | | | | |
|---|---|---|---|---|---|---|
| ggcacgagcg | acgggcccgc | ggggccggcg | ccgccatggc | ggccgtgttt | gatttggatt | 60 |
| tggagacgga | ggaaggcagc | gagggcgagg | gcgagccaga | gctcagcccc | gcggacgcat | 120 |
| gtccccttgc | cgagttgagg | gcagctggcc | tagagcctgt | gggacactat | gaagaggtgg | 180 |
| agctgactga | gaccagcgtg | aacgttggcc | cagagcgcat | cgggccccac | tgctttgagc | 240 |
| tgctgcgtgt | gctgggcaag | gggggctatg | gcaaggtgtt | ccaggtgcga | aaggtgcaag | 300 |
| gcaccaactt | gggcaaaata | tatgccatga | aagtcctaag | gaaggccaaa | attgtgcgca | 360 |
| atgccaagga | cacagcacac | acacgggctg | agcggaacat | tctagagtca | gtgaagcacc | 420 |
| cctttattgt | ggaactggcc | tatgccttcc | agactggtgg | caaactctac | ctcatccttg | 480 |
| agtgcctcag | tggtggcgag | ctcttcacgc | atctggagcg | agagggcatc | ttcctggaag | 540 |
| atacggcctg | cttctacctg | gctgagatca | cgctggccct | gggccatctc | cactcccagg | 600 |
| gcatcatcta | ccgggacctc | aagcccgaga | acatcatgct | cagcagccag | ggccacatca | 660 |
| aactgaccga | ctttggactc | tgcaaggagt | ctatccatga | gggcgccgtc | actcacacct | 720 |
| tctgcggcac | cattgagtac | atggcccctg | agattctggt | gcgcagtggc | cacaaccggg | 780 |
| ctgtggactg | gtggagcctg | ggggccctga | tgtacgacat | gctcactgga | tcgccgccct | 840 |
| ttaccgcaga | gaaccggaag | aaaaccatgg | ataagatcat | cagggggcaag | ctggcactgc | 900 |
| ccccctacct | caccccagat | gcccgggacc | ttgtcaaaaa | gtttctgaaa | cggaatccca | 960 |
| gccagcggat | tgggggtggc | ccaggggatg | ctgctgatgt | gcagagacat | ccctttttcc | 1020 |
| ggcacatgaa | ttggacgac | cttctggcct | ggcgtgtgga | cccccctttc | aggccctgtc | 1080 |
| tgcagtcaga | ggaggacgtg | agccagtttg | atacccgctt | cacacggcag | acgccggtgg | 1140 |
| acagtcctga | tgacacagcc | ctcagcgaga | gtgccaacca | ggccttcctg | ggcttcacat | 1200 |
| acgtggcgcc | gtctgtcctg | gacagcatca | aggagggctt | ctccttccag | cccaagctgc | 1260 |
| gctcacccag | gcgcctcaac | agtagccccc | gggtccccgt | cagcccctc | aagttctccc | 1320 |
| cttttgaggg | gtttcggccc | agcccagcc | tgccggagcc | cacggagcta | cctctacctc | 1380 |
| cactcctgcc | accgccgccg | ccctcgacca | ccgcccctct | cccatccgt | cccccctcag | 1440 |
| ggaccaagaa | gtccaagagg | ggccgtgggc | gtccagggcg | ctaggaagcc | gggtgggggt | 1500 |
| gagggtagcc | cttgagccct | gtccctgcgg | ctgtgagagc | agcaggaccc | tgggccagtt | 1560 |

-continued

```
ccagagacct gggggtgtgt ctgggggtgg ggtgtgagtg cgtatgaaag tgtgtgtctg    1620
ctggggcagc tgtgcccctg aatcatgggc acggagggcc gcccgccaca ccccgcgctc    1680
aactgctccc gtggaagatt aaagggctga atcatgaaaa aaaaaaaaaa aa            1732
```

<210> SEQ ID NO 2
<211> LENGTH: 482
<212> TYPE: PRT
<213> ORGANISM: Homo sapiens

<400> SEQUENCE: 2

```
Met Ala Ala Val Phe Asp Leu Asp Leu Glu Thr Glu Glu Gly Ser Glu
 1               5                  10                  15

Gly Glu Gly Glu Pro Glu Leu Ser Pro Ala Asp Ala Cys Pro Leu Ala
             20                  25                  30

Glu Leu Arg Ala Ala Gly Leu Glu Pro Val Gly His Tyr Glu Glu Val
         35                  40                  45

Glu Leu Thr Glu Thr Ser Val Asn Val Gly Pro Glu Arg Ile Gly Pro
     50                  55                  60

His Cys Phe Glu Leu Leu Arg Val Leu Gly Lys Gly Gly Tyr Gly Lys
 65                  70                  75                  80

Val Phe Gln Val Arg Lys Val Gln Gly Thr Asn Leu Gly Lys Ile Tyr
                 85                  90                  95

Ala Met Lys Val Leu Arg Lys Ala Lys Ile Val Arg Asn Ala Lys Asp
            100                 105                 110

Thr Ala His Thr Arg Ala Glu Arg Asn Ile Leu Glu Ser Val Lys His
        115                 120                 125

Pro Phe Ile Val Glu Leu Ala Tyr Ala Phe Gln Thr Gly Gly Lys Leu
    130                 135                 140

Tyr Leu Ile Leu Glu Cys Leu Ser Gly Gly Glu Leu Phe Thr His Leu
145                 150                 155                 160

Glu Arg Glu Gly Ile Phe Leu Glu Asp Thr Ala Cys Phe Tyr Leu Ala
                165                 170                 175

Glu Ile Thr Leu Ala Leu Gly His Leu His Ser Gln Gly Ile Ile Tyr
            180                 185                 190

Arg Asp Leu Lys Pro Glu Asn Ile Met Leu Ser Ser Gln Gly His Ile
        195                 200                 205

Lys Leu Thr Asp Phe Gly Leu Cys Lys Glu Ser Ile His Glu Gly Ala
    210                 215                 220

Val Thr His Thr Phe Cys Gly Thr Ile Glu Tyr Met Ala Pro Glu Ile
225                 230                 235                 240

Leu Val Arg Ser Gly His Asn Arg Ala Val Asp Trp Trp Ser Leu Gly
                245                 250                 255

Ala Leu Met Tyr Asp Met Leu Thr Gly Ser Pro Pro Phe Thr Ala Glu
            260                 265                 270

Asn Arg Lys Lys Thr Met Asp Lys Ile Ile Arg Gly Lys Leu Ala Leu
        275                 280                 285

Pro Pro Tyr Leu Thr Pro Asp Ala Arg Asp Leu Val Lys Lys Phe Leu
    290                 295                 300

Lys Arg Asn Pro Ser Gln Arg Ile Gly Gly Gly Pro Gly Asp Ala Ala
305                 310                 315                 320

Asp Val Gln Arg His Pro Phe Phe Arg His Met Asn Trp Asp Asp Leu
                325                 330                 335

Leu Ala Trp Arg Val Asp Pro Pro Phe Arg Pro Cys Leu Gln Ser Glu
```

```
                        340             345             350
Glu Asp Val Ser Gln Phe Asp Thr Arg Phe Thr Arg Gln Thr Pro Val
                355                 360                 365

Asp Ser Pro Asp Asp Thr Ala Leu Ser Glu Ser Ala Asn Gln Ala Phe
370                 375                 380

Leu Gly Phe Thr Tyr Val Ala Pro Ser Val Leu Asp Ser Ile Lys Glu
385                 390                 395                 400

Gly Phe Ser Phe Gln Pro Lys Leu Arg Ser Pro Arg Leu Asn Ser
                405                 410                 415

Ser Pro Arg Val Pro Val Ser Pro Leu Lys Phe Ser Pro Phe Glu Gly
                420                 425                 430

Phe Arg Pro Ser Pro Ser Leu Pro Glu Pro Thr Glu Leu Pro Leu Pro
                435                 440                 445

Pro Leu Leu Pro Pro Pro Pro Ser Thr Thr Ala Pro Leu Pro Ile
        450                 455                 460

Arg Pro Pro Ser Gly Thr Lys Lys Ser Lys Arg Gly Arg Gly Arg Pro
465                 470                 475                 480

Gly Arg

<210> SEQ ID NO 3
<211> LENGTH: 495
<212> TYPE: PRT
<213> ORGANISM: Homo sapiens

<400> SEQUENCE: 3

Met Ala Arg Gly Arg Ala Arg Gly Ala Gly Ala Ala Met Ala Ala
  1                 5                  10                  15

Val Phe Asp Leu Asp Leu Glu Thr Glu Glu Gly Ser Glu Gly Glu Gly
                 20                  25                  30

Glu Pro Glu Leu Ser Pro Ala Asp Ala Cys Pro Leu Ala Glu Leu Arg
             35                  40                  45

Ala Ala Gly Leu Glu Pro Val Gly His Tyr Glu Glu Val Glu Leu Thr
         50                  55                  60

Glu Thr Ser Val Asn Val Gly Pro Glu Arg Ile Gly Pro His Cys Phe
65                  70                  75                  80

Glu Leu Leu Arg Val Leu Gly Lys Gly Gly Tyr Gly Lys Val Phe Gln
                 85                  90                  95

Val Arg Lys Val Gln Gly Thr Asn Leu Gly Lys Ile Tyr Ala Met Lys
            100                 105                 110

Val Leu Arg Lys Ala Lys Ile Val Arg Asn Ala Lys Asp Thr Ala His
            115                 120                 125

Thr Arg Ala Glu Arg Asn Ile Leu Glu Ser Val Lys His Pro Phe Ile
        130                 135                 140

Val Glu Leu Ala Tyr Ala Phe Gln Thr Gly Gly Lys Leu Tyr Leu Ile
145                 150                 155                 160

Leu Glu Cys Leu Ser Gly Gly Glu Leu Phe Thr His Leu Glu Arg Glu
                165                 170                 175

Gly Ile Phe Leu Glu Asp Thr Ala Cys Phe Tyr Leu Ala Glu Ile Thr
            180                 185                 190

Leu Ala Leu Gly His Leu His Ser Gln Gly Ile Ile Tyr Arg Asp Leu
        195                 200                 205

Lys Pro Glu Asn Ile Met Leu Ser Ser Gln Gly His Ile Lys Leu Thr
    210                 215                 220

Asp Phe Gly Leu Cys Lys Glu Ser Ile His Glu Gly Ala Val Thr His
```

-continued

```
                225                 230                 235                 240
Thr Phe Cys Gly Thr Ile Glu Tyr Met Ala Pro Glu Ile Leu Val Arg
                245                 250                 255

Ser Gly His Asn Arg Ala Val Asp Trp Trp Ser Leu Gly Ala Leu Met
                260                 265                 270

Tyr Asp Met Leu Thr Gly Ser Pro Pro Phe Thr Ala Glu Asn Arg Lys
                275                 280                 285

Lys Thr Met Asp Lys Ile Ile Arg Gly Lys Leu Ala Leu Pro Pro Tyr
290                 295                 300

Leu Thr Pro Asp Ala Arg Asp Leu Val Lys Lys Phe Leu Lys Arg Asn
305                 310                 315                 320

Pro Ser Gln Arg Ile Gly Gly Gly Pro Gly Asp Ala Ala Asp Val Gln
                325                 330                 335

Arg His Pro Phe Phe Arg His Met Asn Trp Asp Asp Leu Leu Ala Trp
                340                 345                 350

Arg Val Asp Pro Pro Phe Arg Pro Cys Leu Gln Ser Glu Glu Asp Val
                355                 360                 365

Ser Gln Phe Asp Thr Arg Phe Thr Arg Gln Thr Pro Val Asp Ser Pro
                370                 375                 380

Asp Asp Thr Ala Leu Ser Glu Ser Ala Asn Gln Ala Phe Leu Gly Phe
385                 390                 395                 400

Thr Tyr Val Ala Pro Ser Val Leu Asp Ser Ile Lys Glu Gly Phe Ser
                405                 410                 415

Phe Gln Pro Lys Leu Arg Ser Pro Arg Arg Leu Asn Ser Ser Pro Arg
                420                 425                 430

Val Pro Val Ser Pro Leu Lys Phe Ser Pro Phe Glu Gly Phe Arg Pro
                435                 440                 445

Ser Pro Ser Leu Pro Glu Pro Thr Glu Leu Pro Leu Pro Pro Leu Leu
450                 455                 460

Pro Pro Pro Pro Ser Thr Thr Ala Pro Leu Pro Ile Arg Pro Pro
465                 470                 475                 480

Ser Gly Thr Lys Lys Ser Lys Arg Gly Arg Gly Arg Pro Gly Arg
                485                 490                 495

<210> SEQ ID NO 4
<211> LENGTH: 65
<212> TYPE: PRT
<213> ORGANISM: Homo sapiens

<400> SEQUENCE: 4

Met Ala Ala Val Phe Asp Leu Asp Leu Glu Thr Glu Glu Gly Ser Glu
1               5                   10                  15

Gly Glu Gly Glu Pro Glu Leu Ser Pro Ala Asp Ala Cys Pro Leu Ala
                20                  25                  30

Glu Leu Arg Ala Ala Gly Leu Glu Pro Val Gly His Tyr Glu Glu Val
                35                  40                  45

Glu Leu Thr Glu Thr Ser Val Asn Val Gly Pro Glu Arg Ile Gly Pro
        50                  55                  60

His
65

<210> SEQ ID NO 5
<211> LENGTH: 18
<212> TYPE: PRT
<213> ORGANISM: Homo sapiens
```

<400> SEQUENCE: 5

Asp Leu Asp Leu Glu Thr Glu Glu Gly Ser Glu Gly Glu Gly Glu Pro
1               5                   10                  15
Glu Leu

<210> SEQ ID NO 6
<211> LENGTH: 258
<212> TYPE: PRT
<213> ORGANISM: Homo sapiens

<400> SEQUENCE: 6

His Cys Phe Glu Leu Leu Arg Val Leu Gly Lys Gly Tyr Gly Lys
1               5                   10                  15

Val Phe Gln Val Arg Lys Val Gln Gly Thr Asn Leu Gly Lys Ile Tyr
                20                  25                  30

Ala Met Lys Val Leu Arg Lys Ala Lys Ile Val Arg Asn Ala Lys Asp
            35                  40                  45

Thr Ala His Thr Arg Ala Glu Arg Asn Ile Leu Glu Ser Val Lys His
        50                  55                  60

Pro Phe Ile Val Glu Leu Ala Tyr Ala Phe Gln Thr Gly Gly Lys Leu
65                  70                  75                  80

Tyr Leu Ile Leu Glu Cys Leu Ser Gly Gly Glu Leu Phe Thr His Leu
                85                  90                  95

Glu Arg Glu Gly Ile Phe Leu Glu Asp Thr Ala Cys Phe Tyr Leu Ala
                100                 105                 110

Glu Ile Thr Leu Ala Leu Gly His Leu His Ser Gln Gly Ile Ile Tyr
            115                 120                 125

Arg Asp Leu Lys Pro Glu Asn Ile Met Leu Ser Ser Gln Gly His Ile
        130                 135                 140

Lys Leu Thr Asp Phe Gly Leu Cys Lys Glu Ser Ile His Glu Gly Ala
145                 150                 155                 160

Val Thr His Thr Phe Cys Gly Thr Ile Glu Tyr Met Ala Pro Glu Ile
                165                 170                 175

Leu Val Arg Ser Gly His Asn Arg Ala Val Asp Trp Trp Ser Leu Gly
                180                 185                 190

Ala Leu Met Tyr Asp Met Leu Thr Gly Ser Pro Pro Phe Thr Ala Glu
            195                 200                 205

Asn Arg Lys Lys Thr Met Asp Lys Ile Ile Arg Gly Lys Leu Ala Leu
        210                 215                 220

Pro Pro Tyr Leu Thr Pro Asp Ala Arg Asp Leu Val Lys Lys Phe Leu
225                 230                 235                 240

Lys Arg Asn Pro Ser Gln Arg Ile Gly Gly Pro Gly Asp Ala Ala
                245                 250                 255

Asp Val

<210> SEQ ID NO 7
<211> LENGTH: 66
<212> TYPE: PRT
<213> ORGANISM: Homo sapiens

<400> SEQUENCE: 7

Asn Trp Asp Asp Leu Leu Ala Trp Arg Val Asp Pro Pro Phe Arg Pro
1               5                   10                  15

Cys Leu Gln Ser Glu Glu Asp Val Ser Gln Phe Asp Thr Arg Phe Thr
                20                  25                  30

```
Arg Gln Thr Pro Val Asp Ser Pro Asp Asp Thr Ala Leu Ser Glu Ser
         35                  40                  45

Ala Asn Gln Ala Phe Leu Gly Phe Thr Tyr Val Ala Pro Ser Val Leu
 50                  55                  60

Asp Ser
 65

<210> SEQ ID NO 8
<211> LENGTH: 85
<212> TYPE: PRT
<213> ORGANISM: Homo sapiens

<400> SEQUENCE: 8

Ile Lys Glu Gly Phe Ser Phe Gln Pro Lys Leu Arg Ser Pro Arg Arg
 1               5                  10                  15

Leu Asn Ser Ser Pro Arg Val Pro Val Ser Pro Leu Lys Phe Ser Pro
                 20                  25                  30

Phe Glu Gly Phe Arg Pro Ser Pro Ser Leu Pro Glu Pro Thr Glu Leu
             35                  40                  45

Pro Leu Pro Pro Leu Leu Pro Pro Pro Pro Ser Thr Thr Ala Pro
 50                  55                  60

Leu Pro Ile Arg Pro Ser Gly Thr Lys Lys Ser Lys Arg Gly Arg
 65                  70                  75                  80

Gly Arg Pro Gly Arg
                 85

<210> SEQ ID NO 9
<211> LENGTH: 22
<212> TYPE: PRT
<213> ORGANISM: Homo sapiens

<400> SEQUENCE: 9

Pro Leu Pro Pro Leu Leu Pro Pro Pro Pro Ser Thr Thr Ala Pro
 1               5                  10                  15

Leu Pro Ile Arg Pro Pro
             20

<210> SEQ ID NO 10
<211> LENGTH: 65
<212> TYPE: PRT
<213> ORGANISM: Homo sapiens

<400> SEQUENCE: 10

Met Ala Ala Val Phe Asp Leu Asp Leu Glu Thr Glu Glu Gly Ser Glu
 1               5                  10                  15

Gly Glu Gly Glu Pro Glu Leu Ser Pro Ala Asp Ala Cys Pro Leu Ala
                 20                  25                  30

Glu Leu Arg Ala Ala Gly Leu Glu Pro Val Gly His Tyr Glu Glu Val
             35                  40                  45

Glu Leu Thr Glu Thr Ser Val Asn Val Gly Pro Glu Arg Ile Gly Pro
     50                  55                  60

His
 65

<210> SEQ ID NO 11
<211> LENGTH: 18
<212> TYPE: PRT
<213> ORGANISM: Homo sapiens

<400> SEQUENCE: 11
```

-continued

Asp Leu Asp Leu Glu Thr Glu Glu Gly Ser Glu Gly Glu Gly Pro
1               5                   10                  15

Glu Leu

<210> SEQ ID NO 12
<211> LENGTH: 268
<212> TYPE: PRT
<213> ORGANISM: Homo sapiens

<400> SEQUENCE: 12

His Cys Phe Glu Leu Leu Arg Val Leu Gly Lys Gly Tyr Gly Lys
1               5                   10                  15

Val Phe Gln Val Arg Lys Val Gln Gly Thr Asn Leu Gly Lys Ile Tyr
                20                  25                  30

Ala Met Lys Val Leu Arg Lys Ala Lys Ile Val Arg Asn Ala Lys Asp
            35                  40                  45

Thr Ala His Thr Arg Ala Glu Arg Asn Ile Leu Glu Ser Val Lys His
        50                  55                  60

Pro Phe Ile Val Glu Leu Ala Tyr Ala Phe Gln Thr Gly Gly Lys Leu
65                  70                  75                  80

Tyr Leu Ile Leu Glu Cys Leu Ser Gly Gly Glu Leu Phe Thr His Leu
                85                  90                  95

Glu Arg Glu Gly Ile Phe Leu Glu Asp Thr Ala Cys Phe Tyr Leu Ala
                100                 105                 110

Glu Ile Thr Leu Ala Leu Gly His Leu His Ser Gln Gly Ile Ile Tyr
            115                 120                 125

Arg Asp Leu Lys Pro Glu Asn Ile Met Leu Ser Ser Gln Gly His Ile
130                 135                 140

Lys Leu Thr Asp Phe Gly Leu Cys Lys Glu Ser Ile His Glu Gly Ala
145                 150                 155                 160

Val Thr His Thr Phe Cys Gly Thr Ile Glu Tyr Met Ala Pro Glu Ile
                165                 170                 175

Leu Val Arg Ser Gly His Asn Arg Ala Val Asp Trp Trp Ser Leu Gly
                180                 185                 190

Ala Leu Met Tyr Asp Met Leu Thr Gly Ser Pro Pro Phe Thr Ala Glu
            195                 200                 205

Asn Arg Lys Lys Thr Met Asp Lys Ile Ile Arg Gly Lys Leu Ala Leu
        210                 215                 220

Pro Pro Tyr Leu Thr Pro Asp Ala Arg Asp Leu Val Lys Lys Phe Leu
225                 230                 235                 240

Lys Arg Asn Pro Ser Gln Arg Ile Gly Gly Pro Gly Asp Ala Ala
                245                 250                 255

Asp Val Gln Arg His Pro Phe Phe Arg His Met Asn
            260                 265

<210> SEQ ID NO 13
<211> LENGTH: 66
<212> TYPE: PRT
<213> ORGANISM: Homo sapiens

<400> SEQUENCE: 13

Asn Trp Asp Asp Leu Leu Ala Trp Arg Val Asp Pro Pro Phe Arg Pro
1               5                   10                  15

Cys Leu Gln Ser Glu Glu Asp Val Ser Gln Phe Asp Thr Arg Phe Thr
                20                  25                  30

-continued

```
Arg Gln Thr Pro Val Asp Ser Pro Asp Asp Thr Ala Leu Ser Glu Ser
         35                  40                  45

Ala Asn Gln Ala Phe Leu Gly Phe Thr Tyr Val Ala Pro Ser Val Leu
     50                  55                  60

Asp Ser
 65
```

<210> SEQ ID NO 14
<211> LENGTH: 85
<212> TYPE: PRT
<213> ORGANISM: Homo sapiens

<400> SEQUENCE: 14

```
Ile Lys Glu Gly Phe Ser Phe Gln Pro Lys Leu Arg Ser Pro Arg Arg
 1               5                  10                  15

Leu Asn Ser Ser Pro Arg Val Pro Val Ser Pro Leu Lys Phe Ser Pro
             20                  25                  30

Phe Glu Gly Phe Arg Pro Ser Pro Ser Leu Pro Glu Pro Thr Glu Leu
         35                  40                  45

Pro Leu Pro Pro Leu Leu Pro Pro Pro Pro Ser Thr Thr Ala Pro
     50                  55                  60

Leu Pro Ile Arg Pro Pro Ser Gly Thr Lys Lys Ser Lys Arg Gly Arg
 65                  70                  75                  80

Gly Arg Pro Gly Arg
                 85
```

<210> SEQ ID NO 15
<211> LENGTH: 22
<212> TYPE: PRT
<213> ORGANISM: Homo sapiens

<400> SEQUENCE: 15

```
Pro Leu Pro Pro Leu Leu Pro Pro Pro Pro Ser Thr Thr Ala Pro
 1               5                  10                  15

Leu Pro Ile Arg Pro Pro
             20
```

<210> SEQ ID NO 16
<211> LENGTH: 525
<212> TYPE: PRT
<213> ORGANISM: Homo sapiens

<400> SEQUENCE: 16

```
Met Arg Arg Arg Arg Arg Asp Gly Phe Tyr Pro Ala Pro Asp Phe
 1               5                  10                  15

Arg Asp Arg Glu Ala Glu Asp Met Ala Gly Val Phe Asp Ile Asp Leu
             20                  25                  30

Asp Gln Pro Glu Asp Ala Gly Ser Glu Asp Glu Leu Glu Glu Gly Gly
         35                  40                  45

Gln Leu Asn Glu Ser Met Asp His Gly Gly Val Gly Pro Tyr Glu Leu
     50                  55                  60

Gly Met Glu His Cys Glu Lys Phe Glu Ile Ser Glu Thr Ser Val Asn
 65                  70                  75                  80

Arg Gly Pro Glu Lys Ile Arg Pro Glu Cys Phe Glu Leu Leu Arg Val
                 85                  90                  95

Leu Gly Lys Gly Gly Tyr Gly Lys Val Phe Gln Val Arg Lys Val Thr
             100                 105                 110

Gly Ala Asn Thr Gly Lys Ile Phe Ala Met Lys Val Leu Lys Lys Ala
```

```
                    115                 120                 125
Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
    370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
    450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
        515                 520                 525
```